United States Patent
Sperl et al.

(10) Patent No.: US 12,156,793 B2
(45) Date of Patent: Dec. 3, 2024

(54) ABSORBENT ARTICLE WITH PLEATS

(71) Applicant: Kimberly-Clark Worldwide, Inc., Neenah, WI (US)

(72) Inventors: Michael D. Sperl, Waupaca, WI (US); Amanda Lauren Plump, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 706 days.

(21) Appl. No.: 17/298,800

(22) PCT Filed: Dec. 21, 2018

(86) PCT No.: PCT/US2018/067048
§ 371 (c)(1),
(2) Date: Jun. 1, 2021

(87) PCT Pub. No.: WO2020/131096
PCT Pub. Date: Jun. 25, 2020

(65) Prior Publication Data
US 2022/0031524 A1    Feb. 3, 2022

(51) Int. Cl.
*A61F 13/15*   (2006.01)
*A61F 13/49*   (2006.01)
(Continued)

(52) U.S. Cl.
CPC ...... *A61F 13/49001* (2013.01); *A61F 13/494* (2013.01); *A61F 13/51108* (2013.01);
(Continued)

(58) Field of Classification Search
CPC .............. A61F 13/49001; A61F 13/494; A61F 13/51108; A61F 2013/15406; A61F 2013/1591
See application file for complete search history.

(56) References Cited

U.S. PATENT DOCUMENTS 5,746,732 A * 5/1998 Olsson ................ A61F 13/4752
604/385.28
5,906,879 A   5/1999 Huntoon et al.
(Continued)

FOREIGN PATENT DOCUMENTS

AU   2010100851 A4   9/2010
CA      2868911 A1   4/2015
(Continued)

OTHER PUBLICATIONS

Dey, Swatee et al., "Modern diaper performance: construction, materials, and safety review", Jun. 2016, International Journal of Dermatology, http://onlinelibrary.wiley.com/doi/10.1111/ijd.13333/abstract;sessionid=AD0576B6BF81B408A5A567476F4273C6.f03t03.

*Primary Examiner* — Jacqueline F Stephens
(74) *Attorney, Agent, or Firm* — KIMBERLY-CLARK WORLDWIDE, INC.

(57) ABSTRACT

Absorbent articles comprising pleats and methods for forming pleated absorbent articles are disclosed. In one embodiment, an absorbent article extending in a longitudinal direction and a lateral direction may comprise a bodyside liner, an outer cover, an absorbent core disposed between the bodyside liner and the outer cover, and a pleat extending in the longitudinal direction and having a lower pleat portion and an upper pleat portion, the pleat having a pleat height, wherein the lower pleat portion has a greater stiffness than the upper pleat portion.

20 Claims, 17 Drawing Sheets

(51) Int. Cl.
*A61F 13/494* (2006.01)
*A61F 13/511* (2006.01)

(52) U.S. Cl.
CPC .............. *A61F 2013/15406* (2013.01); *A61F 2013/1591* (2013.01)

(56) References Cited

U.S. PATENT DOCUMENTS

| | | | |
|---|---|---|---|
| 6,190,369 B1 | 2/2001 | Palumbo et al. | |
| 6,362,391 B1 | 3/2002 | Mizutani et al. | |
| 6,648,869 B1 * | 11/2003 | Gillies | A61F 13/51104 604/385.19 |
| 6,790,202 B2 * | 9/2004 | Klemp | A61F 13/495 604/385.101 |
| 7,812,213 B2 | 10/2010 | Doverbo et al. | |
| 7,867,210 B2 | 1/2011 | Mori et al. | |
| D634,003 S | 3/2011 | Norman et al. | |
| D639,934 S | 6/2011 | Noel et al. | |
| 8,425,485 B2 * | 4/2013 | Tsuji | A61F 13/5116 604/385.24 |
| D783,812 S | 4/2017 | Kreuzer | |
| D790,689 S | 6/2017 | Noel | |
| 2003/0224146 A1 | 12/2003 | Raidel et al. | |
| 2004/0102752 A1 | 5/2004 | Chen et al. | |
| 2004/0254555 A1 | 12/2004 | Wang et al. | |
| 2005/0288647 A1 | 12/2005 | Ellingson et al. | |
| 2011/0015606 A1 | 1/2011 | Nakajima et al. | |
| 2015/0164706 A1 | 6/2015 | Ben-Natan et al. | |

FOREIGN PATENT DOCUMENTS

| | | |
|---|---|---|
| EP | 1070493 A2 | 1/2001 |
| GB | 2023067 A | 12/1979 |
| JP | 2002336301 A | 11/2002 |
| JP | 2004188115 A | 7/2004 |
| JP | 2009045334 A | 3/2009 |
| JP | 2014226386 A | 12/2014 |
| KR | 20000063004 A | 10/2000 |
| WO | 9960975 A1 | 12/1999 |
| WO | 05063159 A1 | 7/2005 |

* cited by examiner

ABSORBENT ARTICLE WITH PLEATS

TECHNICAL FIELD

The present disclosure relates to absorbent articles, and more specifically to absorbent articles having longitudinally extending pleats.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

One common mode of failure is for exudates to leak out of the leg openings of an absorbent article. As one example, fecal material that is not absorbed or contained by the absorbent article can move over or through any containment features disposed proximate the leg cuffs of the articles and soil or contaminate the wearer's skin and clothing near their legs. This may be more common of an occurrence for semi-solid fecal material, such as low viscosity fecal material, which can be prevalent with younger children. Such exudates can move around on the bodyside liner of an absorbent article under the influence of gravity, motion, and pressure by the wearer of the absorbent article. In such a circumstance, not only does the wearer's absorbent article need to be changed, but the wearer's clothing and/or bedding often also needs to be changed, resulting in additional work, expense, and stress for the caregiver.

Attempts have been made in the past to provide containment systems, especially on the bodyside liner or near the leg cuffs to solve the problems described above. Some examples involve utilizing elasticized containment flaps, having various different structures, to provide better gasketing around a wearer's legs to help prevent leakage. Although such containment flaps have helped to reduce the amount and frequency of leaking, failures still occur. Thus, there is a desire for improvements to absorbent articles to prevent leakage of exudates, especially in the waist regions of the absorbent article.

SUMMARY OF THE DISCLOSURE

The present disclosure relates to absorbent articles, and more specifically to absorbent articles having longitudinally extending pleats.

In one embodiment, an absorbent article may extend in a longitudinal direction and a lateral direction, and the article may comprise a bodyside liner, an outer cover, an absorbent core disposed between the bodyside liner and the outer cover, and a pleat extending in the longitudinal direction and having a lower pleat portion and an upper pleat portion, the pleat having a pleat height, wherein the lower pleat portion has a greater stiffness than the upper pleat portion.

In another embodiment, an absorbent article may extend in a longitudinal direction and a lateral direction, and the article may comprise a bodyside liner, an outer cover, an absorbent core disposed between the bodyside liner and the outer cover, and a pleat material having a first side and a second side and being folded to form a pleat having a folded edge, the pleat material coupled to the bodyside liner with the folded edge disposed away from the bodyside liner and extending generally in the longitudinal direction, wherein the pleat comprises a lower pleat portion and an upper pleat portion and has a pleat height, the pleat material in the lower pleat portion being bonded together and the pleat material in the upper pleat portion being un-bonded. In a further embodiment, an absorbent article may extend in a longitudinal direction and a lateral direction, and the article may comprise a bodyside liner, an outer cover, an absorbent core disposed between the bodyside liner and the outer cover, and a plurality of pleats extending generally in the longitudinal direction, each of the plurality of pleats having a pleat height of between about 2 mm and about 15 mm and spaced a lateral spacing distance from adjacent pleats of between about 2 mm and about 15 mm, wherein each of the plurality of pleats has a lower pleat portion and an upper pleat portion, the lower pleat portion having a greater stiffness than the upper pleat portion.

A method for forming an absorbent article may comprise moving a substrate material having a transverse width dimension in a machine direction, folding the substrate material along a first fold line extending in the machine direction forming a substrate material top layer and a substrate material bottom layer and a first folded transverse material edge, bonding the substrate material top layer to the substrate material bottom layer a bonding distance away from the first folded transverse material edge, unfolding the substrate material, and attaching the substrate material to an absorbent article chassis comprising a back sheet and an absorbent core such that the substrate material sandwiches the absorbent core between the substrate material and the back sheet.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The disclosure may be more completely understood in consideration of the following detailed description of various embodiments in connection with the accompanying drawings, in which.

Figure 1:
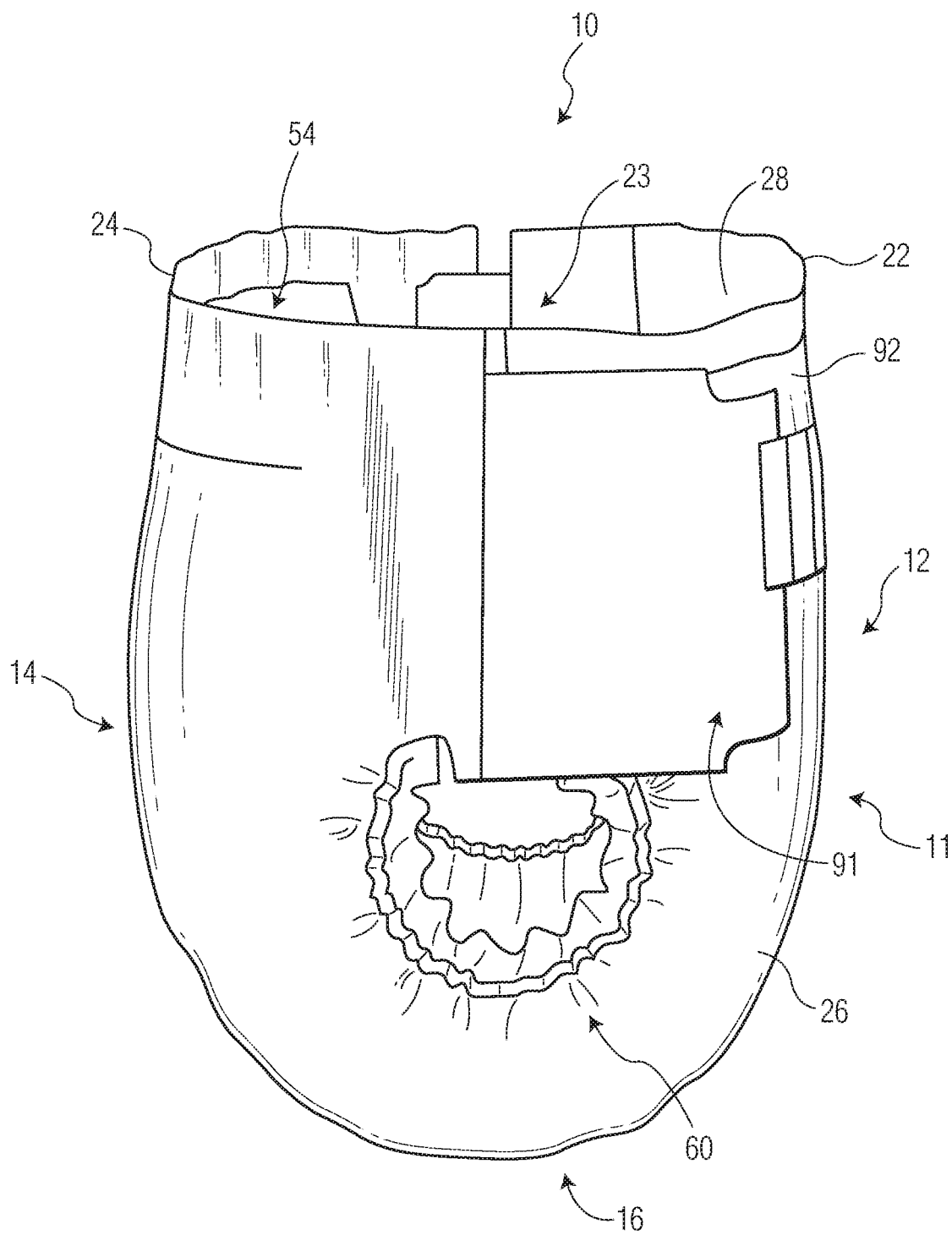
FIG. 1 is side perspective view of an exemplary embodiment of an absorbent article according to aspects of the present disclosure, such as a diaper, in a fastened condition.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION OF THE DISLOSURE

The present disclosure is generally directed toward absorbent articles having longitudinally extending pleats disposed on the body-facing surface of the articles. These longitudinally-extending pleats may act as barriers to liquid and semi-solid fecal material, slowing down outward expansion of such material from an insult point. This slower spreading may allow better uptake of the material into the absorbent core where it is able to be permanently stored, thereby helping to reduce incidents of leakage. The embodiments of the present disclosure detail a number of pleat structures and configurations which are useful in reducing a leakage rate of absorbent articles.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "BM" (i.e., bowel movement) refers to various fecal exudates that are discharged from the anus. BM pads and BM management devices refer to absorbent articles worn adjacent to the anus region that are intended to absorb and contain the various fecal exudates that are discharged from the body.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

FIG. 1 is a perspective view of a non-limiting illustration of an absorbent article 10, for example, a diaper. Other embodiments of absorbent articles according to the present disclosure could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

Figure 2:
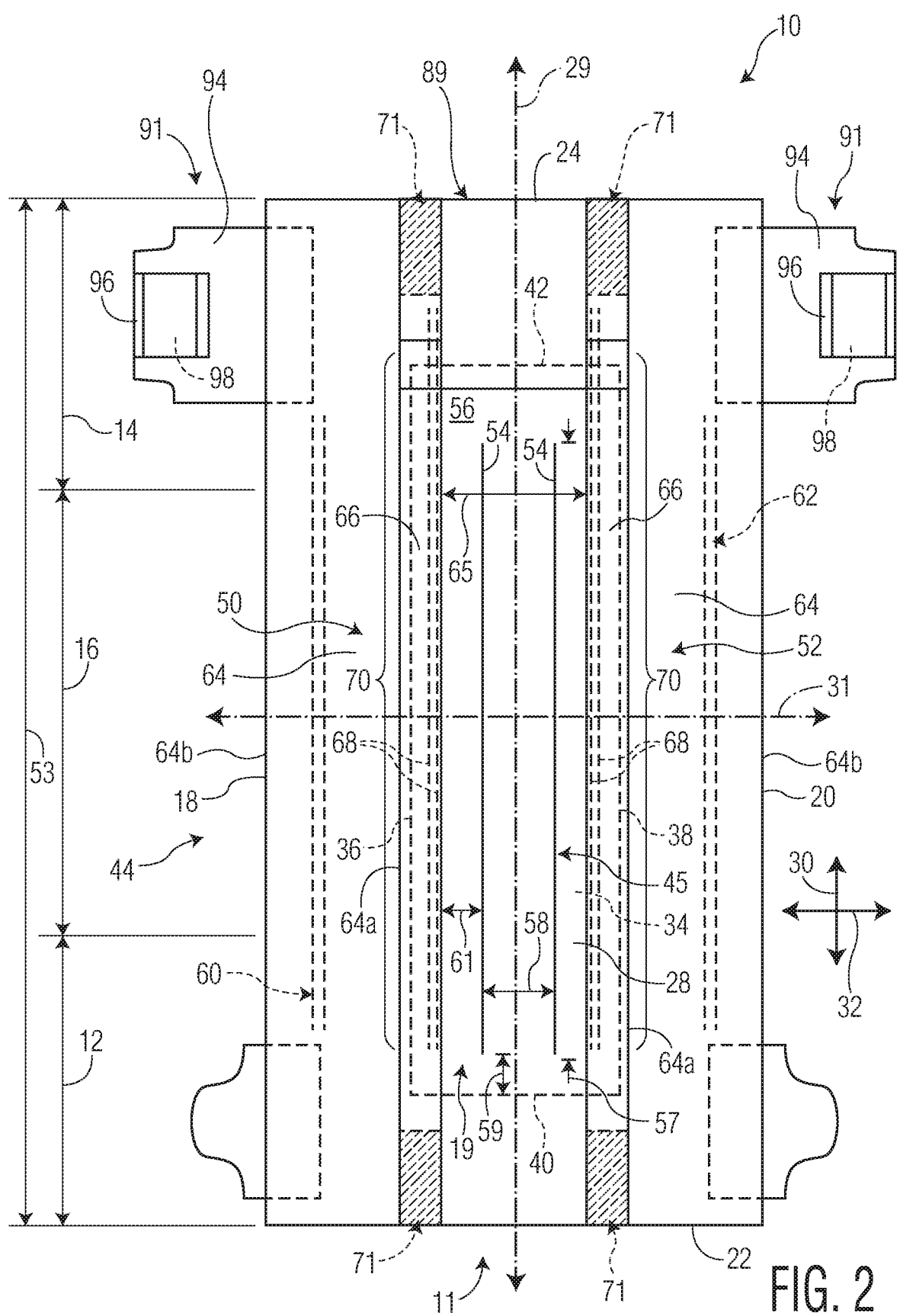
FIG. 2 is an exemplary top plan view of the absorbent article of FIG. 1 in a stretched, laid flat, unfastened condition.

The absorbent article 10 illustrated in FIGS. 1 and 2 can include a chassis 11. The absorbent article 10 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front-end region, the rear waist region 14 can be referred to as the rear-end region, and the crotch region 16 can be referred to as the intermediate region.

The absorbent article 10 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, as depicted in FIG. 2 with respect to article 10. In other embodiments, the longitudinal side edges 18, 20 can be curved between the front waist edge 22 and the rear waist edge 24.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer. The crotch region 16 of the absorbent article 10 can include the portion of the absorbent article 10 that, when worn, is positioned between the legs of the wearer and can partially cover the lower torso of the wearer. The waist edges, 22 and 24, of the absorbent article 10 are configured to encircle the waist of the wearer and together define a central waist opening 23 (as labeled in FIG. 1) for the waist of the wearer. Portions of the longitudinal side edges 18, 20 in the crotch region 16 can generally define leg openings for the legs of the wearer when the absorbent article 10 is worn.

The absorbent article 10 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10. As illustrated in FIG. 2, the absorbent article 10 can have a longitudinal axis 29 extending in the longitudinal direction 30 and a lateral axis 31 extending in the lateral direction 32.

Figure 5:
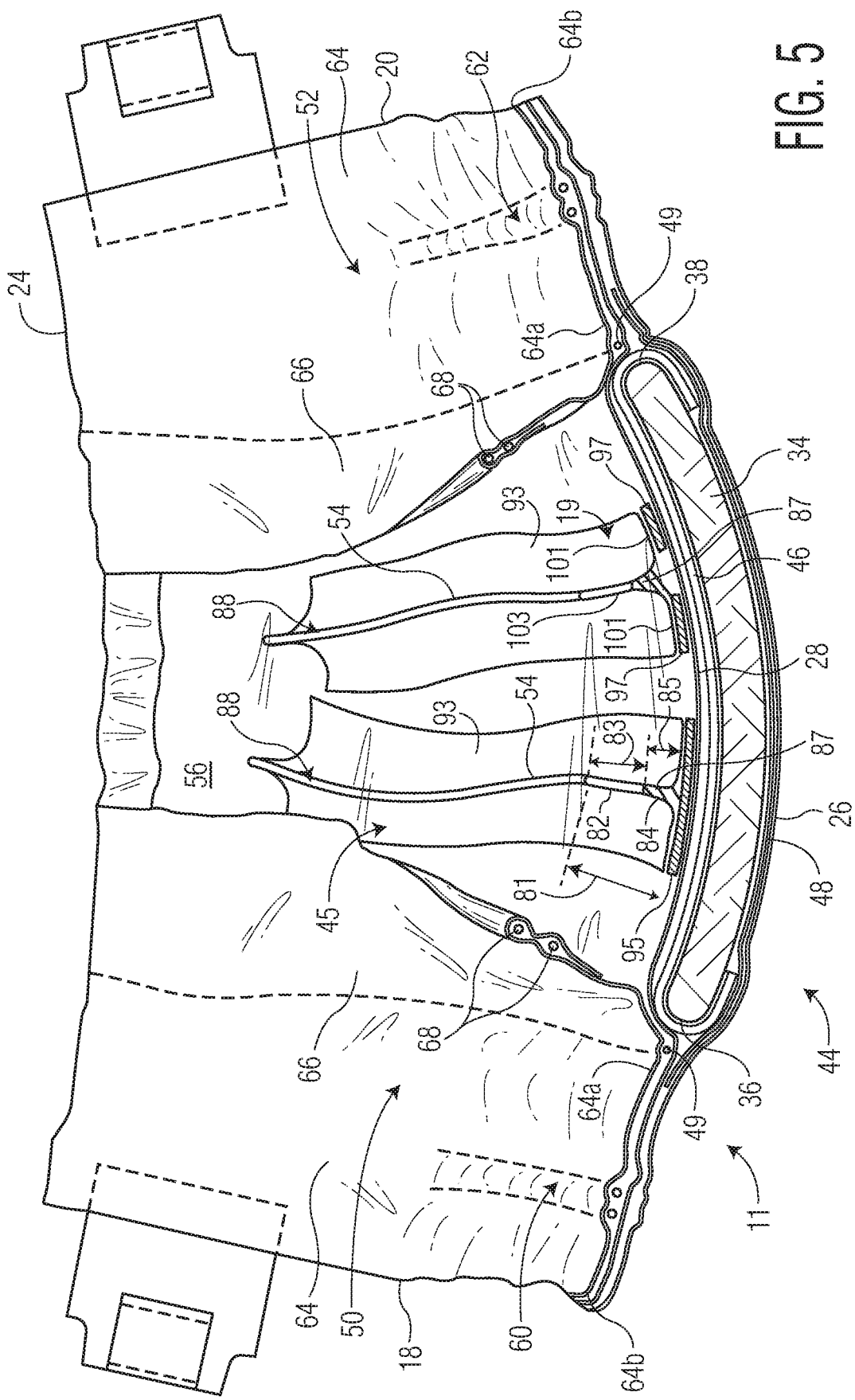
FIG. 5 is a front perspective cross-sectional view taken along lateral axis 31 of an exemplary embodiment of the article 10 from FIG. 2, with the article being in a relaxed configuration.

The chassis 11 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10. The absorbent body 34 can have a first end edge 40 that is opposite a second end edge 42, respectively, which, in an embodiment, can form portions of the waist edges, 22 and 24, respectively, of the absorbent article 10. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10. The bodyside liner 28, the outer cover 26, and the absorbent body 34 can form part of an absorbent assembly 44. The absorbent assembly 44 can also include a fluid transfer layer 46 (as shown in FIG. 5) and a fluid acquisition layer (not shown) between the bodyside liner 28 and the fluid transfer layer 46 as is known in the art. The absorbent assembly 44 can also include a spacer layer 48 (as shown in FIG. 5) disposed between the absorbent body 34 and the outer cover 26.

The absorbent article 10 can be configured to contain and/or absorb liquid, solid, and semi-solid body exudates discharged from the wearer. In some embodiments, containment flaps 50, 52 can be configured to provide a barrier to the lateral flow of body exudates. To further enhance containment and/or absorption of body exudates, the absorbent article 10 can suitably include one or more pleats 54, as will be described in more detail below.

The absorbent article 10 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10. The leg elastic members 60, 62 can be parallel to the longitudinal axis 29 as shown in FIG. 2 or can be curved as is known in the art. The leg elastic members 60, 62 can provide elasticized leg cuffs.

Additional details regarding each of these elements of the absorbent article 10 described herein can be found below and with reference to the FIGS. 1-9.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two-layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web having a basis weight of 30 gsm. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10. The absorbent body 34 can have a length and width that can be less than or equal to the length and width of the absorbent article 10.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

If a spacer layer 48 is present, the absorbent body 34 can be disposed on the spacer layer 48 and superposed over the outer cover 26. The spacer layer 48 can be bonded to the outer cover 26, for example, by adhesive. In some embodiments, a spacer layer 48 may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer 48, can be positioned between the absorbent body 34 and the outer cover 26, such as illustrated in FIG. 5. The absorbent body 34 can be bonded to the fluid transfer layer 46 and/or the spacer layer 48.

Bodyside Liner:

The bodyside liner 28 of the absorbent article 10 can overlay the absorbent body 34 and the outer cover 26 and can isolate the wearer's skin from liquid waste retained by the absorbent body 34. In various embodiments, a fluid transfer layer 46 can be positioned between the bodyside liner 28 and the absorbent body 34. In various embodiments, an acquisition layer (not shown) can be positioned between the bodyside liner 28 and the absorbent body 34 or a fluid transfer layer 46, if present. In various embodiments, the bodyside liner 28 can be bonded to the acquisition layer, or to the fluid transfer layer 46 if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer 46, if present, and/or an acquisition layer, if present, and/or a spacer layer 48, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. It is contemplated that the bodyside liner 28 may be narrower than the outer cover 26. However, in other embodiments, the bodyside liner 28 and the outer cover 26 may be of the same dimensions in width and length. In other embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentangled. The projection layer can include hollow projections, such as those disclosed in U.S. Pat. No. 9,474,660 to by Kirby et al., which is incorporated herein in its entirety.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10. In other aspects, the bodyside liner 28 can be stretchable, and more suitably elastic, in both the lateral and the longitudinal directions 32, 30, respectively.

Containment Flaps:

In an embodiment, the absorbent article 10 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10 through the crotch region 16 to the rear waist region 14 of the absorbent article 10. In some embodiments, the containment flaps 50, 52 can extend in a direction substantially parallel to the longitudinal axis 29 of the absorbent article 10, however, in other embodiments, the containment flaps 50, 52 can be curved, as is known in the art.

In embodiments where the containment flaps 50, 52 are coupled to the chassis 11, the containment flaps 50, 52 can be bonded to the bodyside liner 28 with a barrier adhesive 49, or the containment flaps 50, 52 can be bonded to the outer cover 26 with a barrier adhesive 49 in some embodiments where the bodyside liner 28 does not extend the full lateral width of the outer cover 26. Of course, the containment flaps 50, 52 can be bonded to other components of the chassis 11 and can be bonded with other suitable means other than a barrier adhesive 49. The containment flaps 50, 52 can be constructed of a fibrous material which can be similar to the material forming the bodyside liner 28. Other conventional materials, such as polymer films, can also be employed.

The containment flaps 50, 52 can each include a base portion 64 and a projection portion 66. The base portion 64 can be bonded to the chassis 11, for example, to the bodyside liner 28 or the outer cover 26 as mentioned above. The base portion 64 can include a proximal end 64a and a distal end 64b. The projection portion 66 can be separated from the base portion 64 at the proximal end 64a of the base portion 64. As used in this context, the projection portion 66 is separated from the base portion 64 at the proximal end 64a of the base portion 64 in that the proximal end 64a of the base portion 64 defines a transition between the projection portion 66 and the base portion 64. The proximal end 64a of the base portion 64 can be located near the barrier adhesive 49. In some embodiments, the distal ends 64b of the base portion 64 can laterally extend to the respective longitudinal side edges 18, 20 of the absorbent article 10. In other embodiments, the distal ends 64b of the base portion 64 can end laterally inward of the respective longitudinal side edges 18, 20 of the absorbent article 10. The containment flaps 50, 52 can also each include a projection portion 66 that is configured to extend away from the body facing surface 19 of the chassis 11 at least in the crotch region 16 when the absorbent article 10 is in a relaxed configuration, as illustrated in FIG. 5. The containment flaps 50, 52 can include a tack-down region 71 in either or both of the front waist region 12 and the rear waist region 14 where the projection portion 66 is coupled to the body facing surface 19 of the chassis 11.

It is contemplated that the containment flaps 50, 52 can be of various configurations and shapes, and can be constructed by various methods. For example, the containment flaps 50, 52 of depict a vertical containment flap 50, 52 with a tack-down region 71 in both the front and rear waist regions 12, 14 where the projection portion 66 of each containment flap 50, 52 is tacked down to the bodyside liner 28 towards or away from the longitudinal axis 29 of the absorbent article 10. However, the containment flaps 50, 52 can include a tack-down region 71 where the projection portion 66 of each of the containment flaps 50, 52 is folded back upon itself and coupled to itself and the bodyside liner 28 in a "C-shape" configuration, as is known in the art and described in U.S. Pat. No. 5,895,382 to Robert L. Popp et al. As yet another alternative, it is contemplated that the containment flaps 50, 52 could be constructed in a "T-shape" configuration, such as described in U.S. Pat. No. 9,259,362 by Robert L. Popp et al. Such a configuration can also include a tack-down region 71 in either or both of the front and rear waist regions 12, 14, respectively. Of course, other configurations of containment flaps 50, 52 can be used in the absorbent article 10 and still remain within the scope of this disclosure.

The containment flaps 50, 52 can include one or more flap elastic members 68, such as the two flap elastic strands depicted in FIG. 2. Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIG. 2, can have two strands of elastomeric material extending longitudinally in the projection portion 66 of the containment flaps 50, 52, in generally parallel, spaced relation with each other. The elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, when the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. The elastic members 68 can be coated with adhesive while elongated to a specified length prior to attaching to the elastic members 68 to the containment flaps 50, 52. In a stretched condition, the length of the elastic members 68 which have adhesive coupled thereto can provide an active flap elastic region 70 in the containment flaps 50, 52 which will gather upon relaxation of the absorbent article 10. The active flap elastic region 70 of containment flaps 50, 52 can be of a longitudinal length that is less than the length of the absorbent article 10. In this exemplary method of bonding the elastic members 68 to the containment flaps 50, 52, the portion of the elastic members 68 not coated with adhesive will retract after the elastic members 68 and the absorbent article 10 are cut in manufacturing to form an individual absorbent article 10. As noted above, the relaxing of the elastic members 68 in the active flap elastic region 70 when the absorbent article 10 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 56 of the bodyside liner 28), as depicted in FIG. 5.

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28 as depicted in FIG. 5, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10 without departing from the scope of this disclosure.

Fastening System:

In an embodiment, the absorbent article 10 can include a fastening system. The fastening system can include one or more back fasteners 91 and one or more front fasteners 92. The embodiments shown in FIG. 1 depict embodiments with one front fastener 92. Portions of the fastening system may be included in the front waist region 12, rear waist region 14, or both.

The fastening system can be configured to secure the absorbent article 10 about the waist of the wearer in a fastened condition as shown in FIG. 1 and help maintain the absorbent article 10 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in one example shown in FIG. 2.

Pleats:

In various embodiments, the absorbent article 10 can have one or more pleats 54 disposed on the body facing surface 19 which extend generally in the longitudinal direction 30. In the embodiment of FIG. 2, the article 10 has two pleats 54 extending in the longitudinal direction 30. The pleats 54 may help to resist or slow lateral spread of liquid and/or semi-solid fecal material from an initial insult point toward the containment flaps 50, 52. This relatively slower expansion allows for increased time for the absorbent body 34 to absorb the liquid and/or material prior to it reaching the containment flaps 50, 52, thereby helping to prevent leakage at the flaps 50, 52.

In the embodiment of FIG. 2, the pleats 54 may extend for a longitudinal length 57. The longitudinal length 57 may be between about 25% and about 100% of the overall longitudinal length 53 of the chassis 11. The pleats 54 may generally extend through at least the crotch region 16 or at least through the rear waist region 14. In some embodiments, the pleats 54 may extend through a portion of both the rear waist region 14 and the crotch region 16, and through portions of the front waist, rear waist and crotch regions 12, 14, and 16 in still other embodiments. In more specific embodiments, the longitudinal length 57 may be between about 25% and about 80%, or between about 40% and about 70% of the overall longitudinal length 53 of the chassis 11. In still further embodiments, the length 57 of the pleats 54 may coincide with a longitudinal length of the absorbent body 34. Although, in other embodiments, the pleats 54 may extend longitudinally for a length that is less than the length of the absorbent body 34 and where ends of the pleats 54 are disposed a distance 59 from end edges 40, 42 of the absorbent body. The distance 59 may be between about 1% and about 20% of the length of the absorbent body 34. It has been found that pleats 54 having any of the above described lengths and positioning are disposed in optimal positions with regard to where fecal material insults most commonly occur in the article 10, thereby helping to provide the greatest benefit in helping to prevent leakage by slowing down the fecal material spread.

The pleats 54 may be disposed a spacing distance 58 from each other. In the embodiment of FIG. 2 where the article 10 comprises two pleats 54, the pleats 54 may generally be disposed on opposite sides of the longitudinal axis 29. The pleats 54 may be symmetrically disposed on opposite sides of the longitudinal axis 29, but this is not necessary in all embodiments. The spacing distance 58 may be between about 25% and about 75% of the distance 65 between projection portions 66 of the containment flaps 50, 52 (as measured when the article 10 is in an open, stretched, and laid flat configuration). In more specific embodiments, the spacing distance 58 may be between about 40% and about 60% of the distance 65. The distance between the pleats 54 and the projection portions 66 of the containment flaps 50, 52 is defined as distance 61. It may be desirable for the pleats 54 to be spaced at least a minimum distance from the projection portions 66. The minimum value for distance 61 may be the height of the pleats 54. In this manner, the pleats 54 may not fold over onto the body-facing surface 19 of the chassis 11 and bridge over the projection portions 66 of the containment flaps 50, 52 to prevent an effective gasket from being formed between the containment flaps 50, 52 and the wearer's body.

Figure 3:
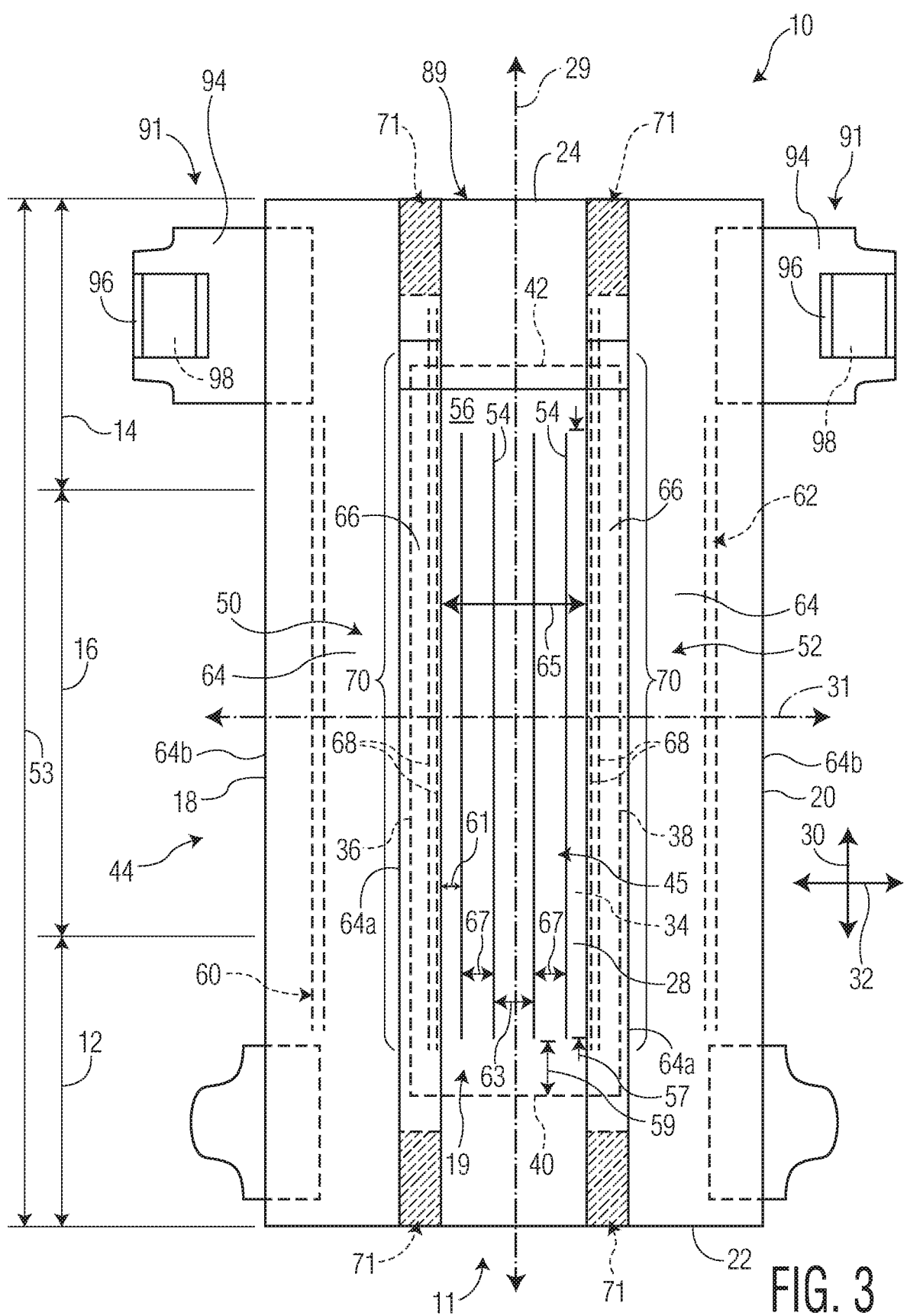
FIG. 3 is another exemplary top plan view of the absorbent article of FIG. 1 in a stretched, laid flat, unfastened condition.
Figure 4:
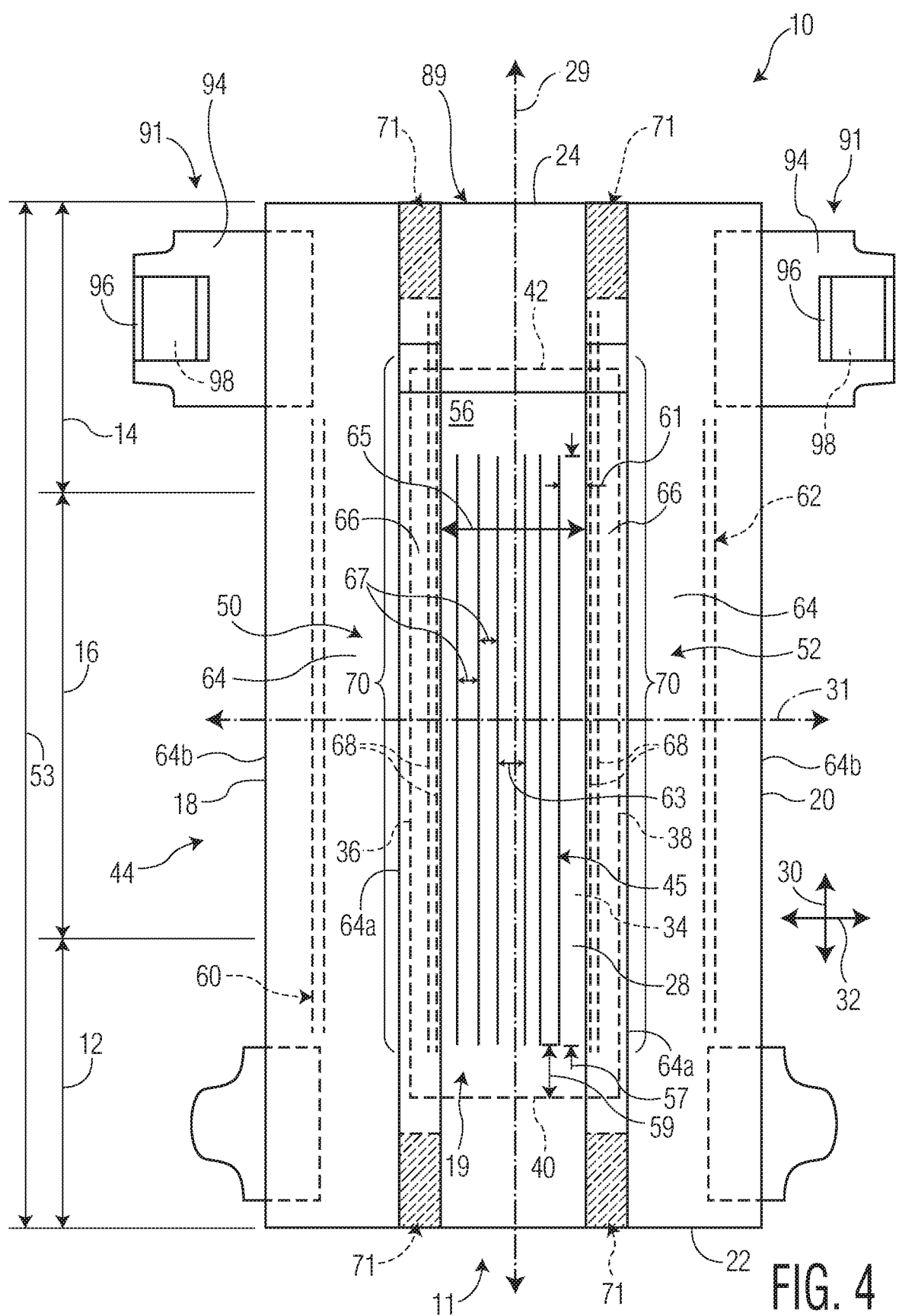
FIG. 4 is a further exemplary top plan view of the absorbent article of FIG. 1 in a stretched, laid flat, unfastened condition.

Further embodiments contemplated by the present disclosure may comprise different numbers of pleats 54. For example, FIGS. 3 and 4 depict alternate embodiments of absorbent article 10 having four (4) pleats 54 and six (6) pleats 54, respectively. It should be understood that these depicted embodiments are not meant to be limiting. In general, contemplated embodiments may include any suitable number of pleats 54, such greater than about one (1) and less than about twenty (20). Additionally, although the depicted embodiments of FIGS. 2, 3, and 4 show an even number of pleats 54, further contemplated embodiments may have an odd number of pleats 54.

In the embodiments of FIGS. 3 and 4, the pleats 54 may be spaced differently in different embodiments. Specifically, the pleats 54 disposed on a same side of the longitudinal axis 29 may be spaced a distance 67, while adjacent pleats 54 disposed on opposite sides of the longitudinal axis 29 may be spaced a distance 63. In some embodiments, the distances 63, 67 may be equal such that there is even spacing between each of the pleats 54. In other embodiments, the distance 63 may range between about 5% and about 45% of the distance 65. The distance 67 may range between about 5% and about 40% of the distance 65. In some specific embodiments with absorbent article 10 having dimensions common for diapers, the distance 63, 67 may preferably be between about 4 mm and about 15 mm, or between about 6 mm and about 12 mm.

Although shown as extending in parallel with each other, the pleats 54 do not need to be parallel in all embodiments. In other embodiments, the pleats 54 may be angled with respect to adjacent pleats 54, or the pleats 54 may have varying levels of curvature. In such embodiments, the distances 63, 67 may be measured anywhere along the lengths of the pleats 54. For example, in embodiments where adjacent pleats 54 are angled with respect to each other, the adjacent pleats 54 may be considered to be spaced a distance 63 or 67 that falls within the above described ranges if the distance 63 or 67 falls within the described ranges at some point along the lengths of the adjacent pleats, as measured in a direction parallel to the lateral axis 31. As one example, two adjacent pleats 54 may be disposed on the same side of the longitudinal axis 29 and be spaced apart a distance 67. At one point along their lengths, the distance 67 may be 2 mm. At another point along their lengths, the distance 67 may be 20 mm. Where these adjacent pleats 54 are continuous along their length, then at some point along their lengths the adjacent pleats 54 will be spaced a distance 67 that falls within the range of about 4 mm and about 15 mm. Accordingly, in such embodiments, the adjacent pleats 54 will be considered to be spaced a distance 67 that is between about 4 mm and about 15 mm.

In some embodiments, the pleats 52 may be configured to optimally effective at managing urine flow through the absorbent article 10. In such embodiments, the pleats 54 may be spaced closer together than between about 4 mm and about 15 mm. This spacing may be desirable for managing BM flow and may need such large spacing to allow for the BM to penetrate between the pleats down to the body-facing surface 45 of the absorbent assembly 44. In embodiments where the pleats 52 are configured for urine management, the distances 63, 67 may be between about 1 mm and about 6 mm, or between about 2 mm and about 5 mm, or between about 2 mm and about 4 mm. In embodiments directed toward urine management, it may be desirable for the number of pleats 52 to be relatively high, for example between about eight (8) and about twenty (20), or between about twelve (12) and about twenty (20).

FIG. 5 is a cross-section view of the article 10 of FIG. 2 as viewed along line 5-5 depicting the cross-sectional structure of the pleats 54. In the specific embodiment of FIG. 5, each of the pleats 54 may be formed from a separate pleat material 93. The pleat material 93 may be folded to form the pleat 54, with the fold 88 in the material 93 forming an edge of the pleat 54 disposed away from the body facing surface 19 of the chassis 11. The pleat material 93 may be bonded to the liner 28 by a continuous bond 95, as shown in the left-hand pleat 54 in FIG. 5. The continuous bond 95 may extend under both the base portions 101 of the pleat material 93 and under the projection portion 103. In other embodiments, the pleat material 93 may be bonded to the liner 28 by multiple, discontinuous bonds 97, as shown in the right-hand pleat 54 in FIG. 5. Each of the bonds 97 may be disposed on either side of the projection portion 103 and bond the base portions 101 of the pleat material 93 to the liner 28. The bonds 95 and/or 97 may be formed by adhesive or by heat and/or pressure or with the use of ultrasonic energy, all of which techniques are all well-known in the art. Although shown as solid bonds, the bonds 95, 97 may form any suitable pattern, such as continuous or intermittent, or points/beads, or swirls, or the like.

The pleat material 93 may comprise a variety of materials in different embodiments. In some embodiments, the pleat material 93 can be comprised of a spunbond-meltblown-spunbond ("SMS") material. However, it is contemplated that the pleat material 93 can be comprised of other materials including, but not limited to, a bonded carded web ("BOW"), or any non-woven material. In other embodiments, the pleat material 93 can be comprised of a laminate of more than one of these exemplary materials, or other materials. The basis weight of the pleat material 93 can vary, however, in some preferred embodiments the basis weight can be between about 5 gsm to about 150 gsm. More preferably, the basis weight of the pleat material 93 can be between about 10 gsm to about 60 gsm, and even more preferably, between about 15 gsm to about 65 gsm. In still further embodiments, the pleat material 93 may be formed from any materials described above with respect to liner 28.

The pleats 54 may have a pleat height 81. The pleat height 81 may be between about 4 mm and about 15 mm, or between about 6 mm and about 12 mm. Through analytical testing, it has been found that these heights produce good results in helping to prevent and/or slow the spread of liquid and/or fecal material toward the containment flaps 50, 52 thereby helping to prevent leakage. For example, in one experiment absorbent articles according to embodiments of the present disclosure having differing pleat configurations were tested for to failure (e.g. identification of leakage) and the applied material load (in mL) was recorded at first sign of failure. In the test, an artificial BM material was applied at a common insult point in each of the articles. The amount of applied artificial BM material was recorded upon first detection of leakage of the BM material—that is identification of the BM material spreading beyond the containment flaps 50, 52 or the rear waist edge 24. A sample size of ten (10) articles per pleat configuration were used, with five (5) of the ten (10) articles of each sample tested on a mannequin disposed in a supine position and the other five (5) articles tested on a mannequin disposed in a car-set position. The below table indicates that the articles with 6 mm spacing performed the best.

TABLE 1

| Article Pleat Configuration - [Number of Pleats, Pleat Spacing (in mm), Pleat Height (in mm)] | Least Square Means of the Average BM Simulant Load at Leak (in mL) |
|---|---|
| [0, 0, 0] | 135 |
| [14, 6, 6] | 190.5 |
| [14, 6, 12] | 156 |
| [7, 12, 6] | 156 |
| [7, 12, 12] | 138 |

As can be seen by the test results, a number of the pleat configurations performed significantly better at containing more of the artificial BM material before leaking than the control product (listed as the [0, 0, 0] configuration above). In particular, the samples having pleats having pleat spacings and/or pleat heights of between about 6 mm and about 12 mm improved the ability of the articles 10 to hold between about 15% and about 41% more artificial BM material prior to failure (e.g. identification of leakage of the BM material).

Of course, the pleat heights 81 of each of the pleats 54 may not necessary need to be the same. According to some contemplated embodiments of the present disclosure, the pleat heights 81 of the pleats 54 located closer to the longitudinal axis 29 may be greater than the pleat heights 81 of the pleats 54 located further away from the longitudinal axis 29. In some particular embodiments, the pleat heights 81 of the pleats 54 may decrease the further away a pleat 54 is from the longitudinal axis 29. For example, a pleat 54 disposed closest to the longitudinal axis 29 may have a pleat height 81 of 12 mm, while a pleat disposed further away from the longitudinal axis 29 may have a pleat height of 4 mm. The other pleats 54 disposed between these identified pleats may have pleat heights less than 12 mm and greater than 4 mm. Although, in other embodiments the pleat heights 81 may increase as the pleats 54 are disposed further away from the longitudinal axis 29. For example, a pleat 54 disposed closest to the longitudinal axis 29 may have a pleat height 81 of 4 mm, while a pleat disposed further away from the longitudinal axis 29 may have a pleat height of 12 mm. The other pleats 54 disposed between these identified pleats may have pleat heights greater than 4 mm and less than 12 mm.

In some embodiments, it may be beneficial for the pleats 54 to have a differing level of stiffness between the pleat upper portion 82 and the pleat lower portion 84, with the lower pleat portion 84 being stiffer than the upper pleat portion 82. It has been found that having such a differing level of stiffness is helpful in preventing and/or slowing the spread of liquid and/or fecal material toward the containment flaps 50, 52. Such a stiffness differential may be beneficial for other reasons, such as comfort—the stiffer, lower pleat portion 84 allows for resistance to liquid and/or fecal material spread, while the less-stiff, upper pleat portion 82 is softer and more comfortable for a wearer.

In embodiments where the pleats 54 comprise a differing level of stiffness between the pleat upper portion 82 and the pleat lower portion 84, the difference in stiffness may be achieved in different manners. In some embodiments, a portion of the projection portion 103 of the pleat material 93 may be bonded together by a bond 87. Such a bonded region may define the extent of the lower pleat portion 84. The upper pleat portions 82 may then be defined as the un-bonded portion of the pleats 54. The portion 82 being un-bonded may provide for a lower level of stiffness as compared to the bonded lower pleat portion 84.

In some of these embodiments, the bond 87 may be achieved with adhesive. Suitable adhesives may comprise any known construction adhesive commonly used in absorbent articles. The adhesive may be applied at a basis weight of between about 0.5 gsm and about 5.0 gsm when using a component web having a basis weight between about 5.0 gsm and about 150 gsm to achieve the desired stiffness levels. In further embodiments, instead of using an adhesive to form the bond 87, the bond 87 may comprise a mechanical bond formed by heat and/or pressure or with the use of ultrasonic energy.

Bonding the two sides of the projection 103 together fashion can achieve the desired differing level of stiffness between the upper pleat portion 82 and the lower pleat portion 84. Although, in still other embodiments, the pleat material 93 may be formed in such a manner as to have regions of greater stiffness and regions of lower stiffness. In these embodiments, the material 93 may be folded such that the regions of greater stiffness form the lower pleat portions 84 while the regions of less stiffness form the upper pleat portions 82.

The pleat portions 82, 84 may have differing heights in different embodiments. In some specific embodiments, the lower pleat portion may have a lower pleat portion height 85 that is greater than about 5% of the pleat height 81 and less than about 100% of the pleat height 81, or between about 15% and about 95%, or between about 25% and about 95%, or between about 25% and about 75% of the pleat height 81. The upper pleat portion 82 will then have a corresponding upper pleat portion height 83 in these embodiments—for instance greater than about 5% and less than about 100% of the pleat height 81, or between about 5% and about 85%, or between about 5% and about 75%, or between about 25% and about 75% of the pleat height 81, respectively.

Figure 6:
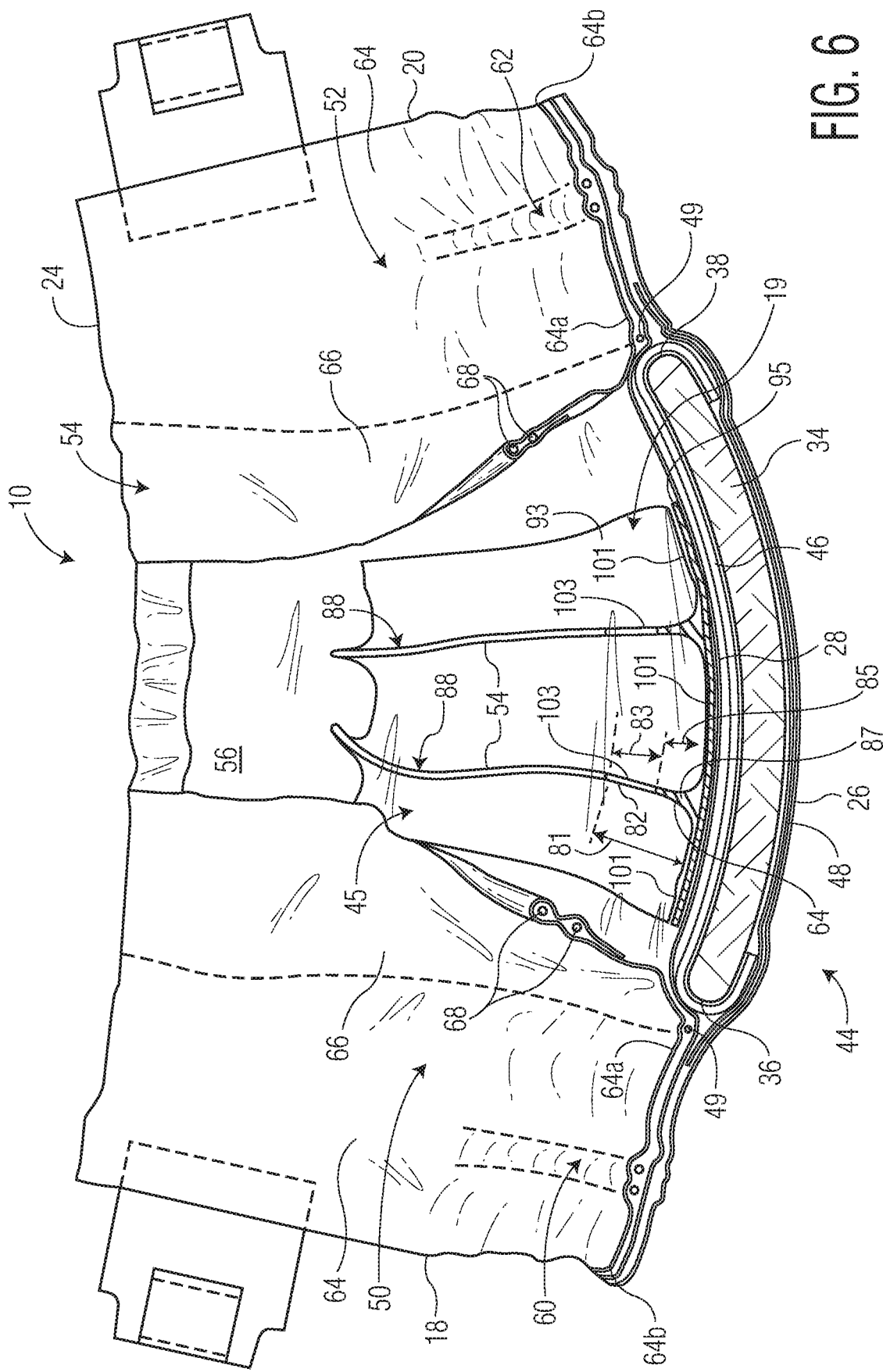
FIG. 6 is a front perspective cross-sectional view taken along lateral axis 31 of another exemplary embodiment of the article 10 from FIG. 2, with the article being in a relaxed configuration.

Of course, the pleats 54 do not need to be made from individual pleat materials 93 in all embodiments. Some embodiments contemplated by the present disclosure include those where all the pleats 54 are formed from a single pleat material 93, as shown in FIG. 6. FIG. 6 depicts a cross-section view of the article 10 of FIG. 2 as viewed along line 5-5 of an alternative configuration as shown in FIG. 5. The singular pleat material 93 may be folded multiple times, thereby forming multiple folds 88 which comprise the pleats 54. The singular pleat material 93 may be bonded to the liner 28 by bond 95. The bond 95 may be formed by adhesive or by heat and/or pressure or with the use of ultrasonic energy, all of which techniques are all well-known in the art. Although shown as a solid bond, the bond 95 may form any suitable pattern, such as continuous or intermittent, or points/beads, or swirls, or the like.

Figure 7:
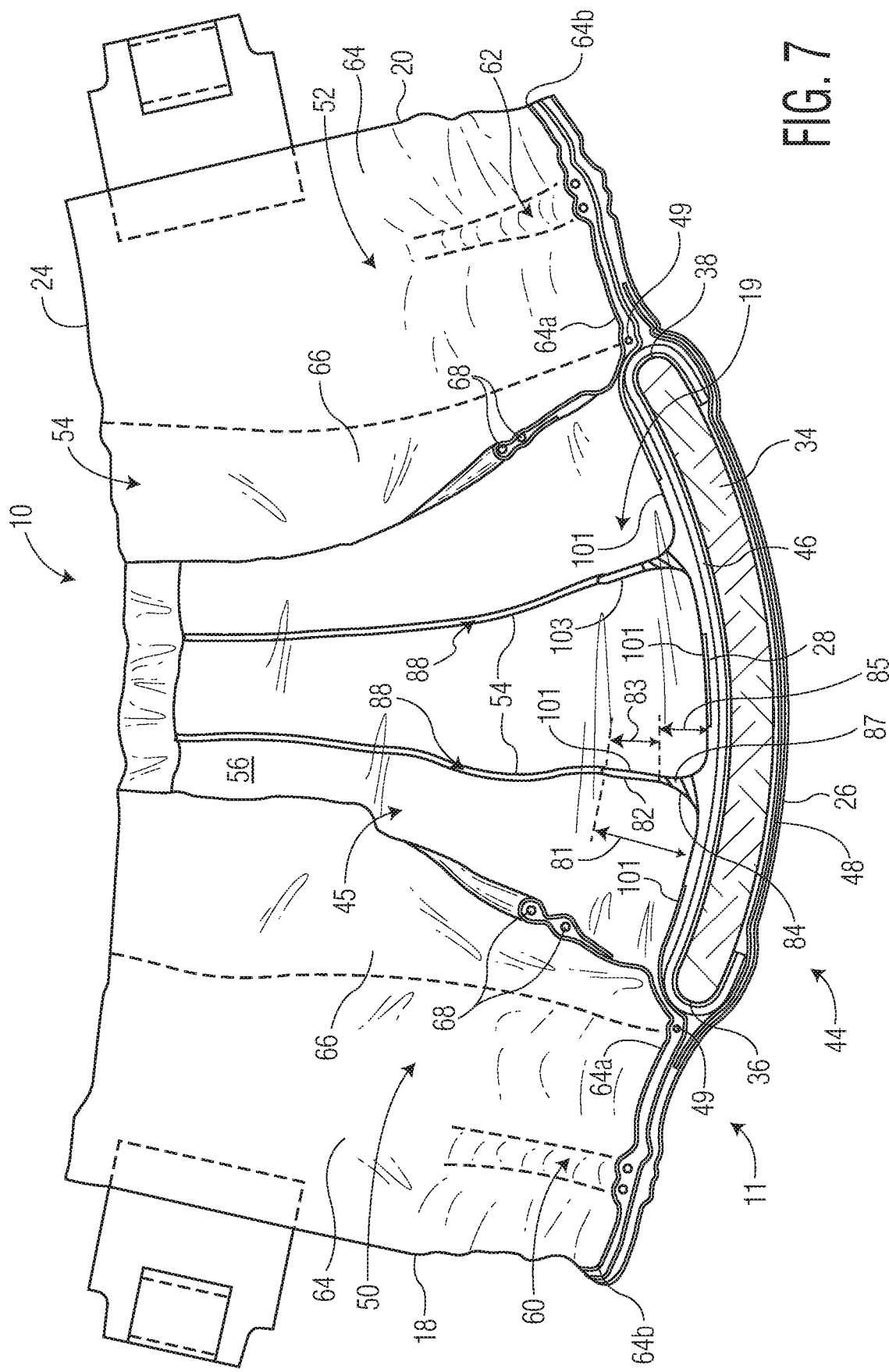
FIG. 7 is a front perspective cross-sectional view taken along lateral axis 31 of further exemplary embodiment of the article 10 from FIG. 2, with the article being in a relaxed configuration.

FIG. 7 is a cross-section view of the article 10 of FIG. 2 as viewed along line 5-5 depicting yet another exemplary embodiment of a contemplated cross-sectional structure of the pleats 54 according to aspects of the present disclosure. In the embodiment of FIG. 7, instead of being formed from a separate pleat material 93, the pleats 54 may be formed directly from the liner 28. In such embodiments, the liner 28 may be folded to comprise folds 88 which form the pleats 54 prior to application of the liner 28 to the chassis 11. In such embodiments, the pleats 54 may extend for the full longitudinal length of the liner 28. In still further embodiments, the pleats 54 may be formed in both the liner 28 and the fluid transfer layer 46. In even further embodiments, the pleats 54 may be formed in the liner 28, the fluid transfer layer 46, and in a core wrap material. More generally, the pleats 54 may be formed in any combination of, or all of, the layers of material disposed on top of the absorbent body 34.

In yet another embodiment, ends of the pleats 54 may be tacked down to the body-facing surface 45 of the absorbent assembly 44, for example similarly to the projection portions 66 of the containment flaps 50, 52 in tack down regions 71. In such embodiments, a portion of end regions of the pleats 54 may be bonded to the body-facing surface 45 of the absorbent assembly 44 such as with adhesive or through mechanical bonds. Such tacked-down ends of the pleats 54 may form miniature pockets which can help contain bodily exudates, thereby helping to prevent the spread of the exudates in an effort to decrease leakage of the articles 10. These particular embodiments may be particularly suitable for pleats 54 having pleat heights that are between about 6 mm and about 15 mm, or between about 8 mm and about 15 mm.

Figure 8:
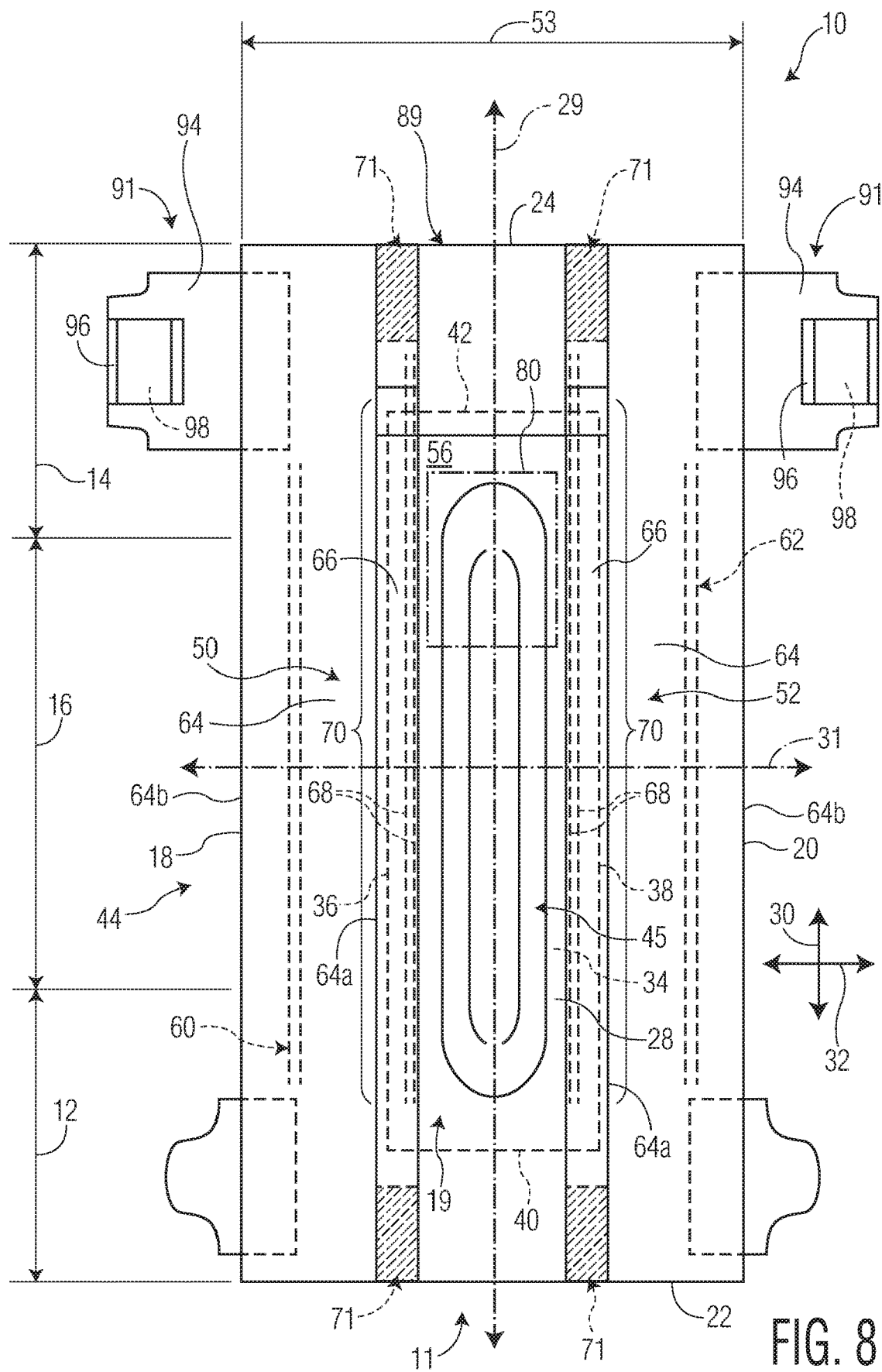
FIG. 8 is a further exemplary top plan view of the absorbent article of FIG. 1 in a stretched, laid flat, unfastened condition.
Figure 9:
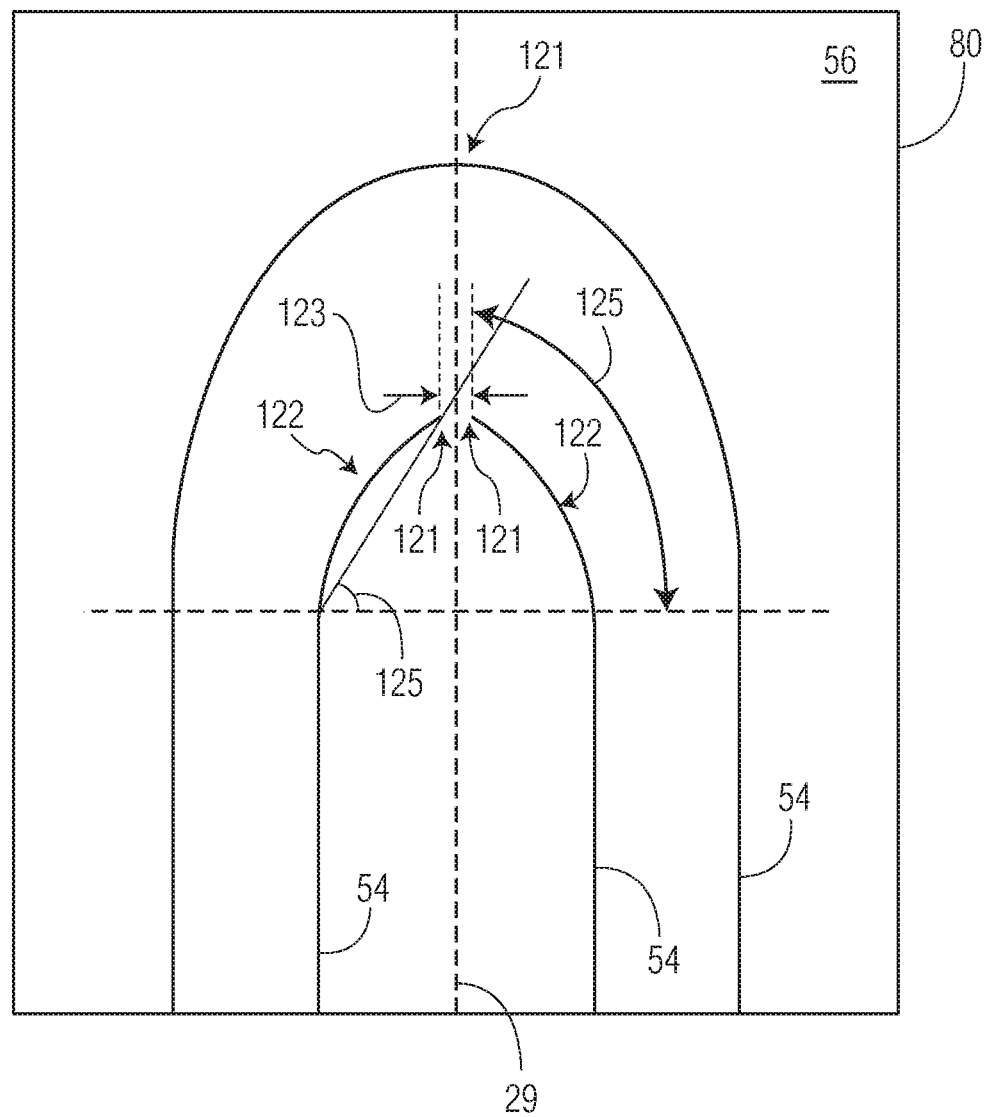
FIG. 9 is a close-up of the region 80 of FIG. 8 depicting details of pleats of the article shown in FIG. 8, according to aspects of the present disclosure.

FIG. 8 depicts another exemplary embodiment of article 10 in which the pleats 54 comprise angled or curved portions. FIG. 9 depicts a close-up of region 80 of FIG. 8, showing the details of angled or curved portions 122 in more detail. Accordingly, as can be seen in FIGS. 8 and 9, it is not necessary in all embodiments for the pleats 54 to extend in a substantially straight manner, as shown with respect to the other FIGS. 2-7. Additionally, although shown as curving in FIGS. 8 and 9, it should be understood that portions of the pleats 54 may be angled instead of curved in other embodiments.

In general, where the pleats 54 comprise angled or curved portions 122, it may be beneficial for the portions 122 to be disposed along end regions of the pleats 54. For example, the angled or curved portions 122 may be the portions of the pleats 54 disposed proximate the rear waist region 14 in some embodiments, or proximate the front waist region 12 in other embodiments. In still further embodiments, the pleats 54 may comprise angled or curved portions 122 comprising the portions of the pleats 54 disposed in both the front and rear waist regions 12, 14. According to some aspects of the present disclosure, the angled or curved portions 122 may comprise the front and/or rear most portions of the pleats 54 and have lengths 125 which are between about 1% and about 35%, or between about 1% and about 20%, of the overall lengths of the pleats 54.

Where the pleats 54 include angled or curved portions 122, the angled or curved portions 122 may define an angle 127 between where the angled or curved portions 122 start and the pleat ends 121. For example, a line may be drawn through a pleat end 121 and a point long the pleat 54 where the angled or curved portions 122. The angle 127 may be the angle formed between such a line and the lateral direction 32. Some suitable ranges of values for the angle 127 may be between about 35 degrees and about 85 degrees, or between about 40 degrees and about 80 degrees, or between about 45 degrees and about 75 degrees.

The pleat ends 121 may have a varied spacing 123 in different embodiments. In some embodiments it may be beneficial for the pleats 54 to angle or curve toward each other. Generally, the positioning of the pleats 54 may act to direct at least some of the bodily exudates along the pleats 54. By angling or curving portions of the pleats 54, the bodily exudates may be directed toward desired locations of the body-facing surface 45 of the absorbent assembly 44. In some particular embodiments, the article 10 may comprise a waist containment member (not shown) which comprises a pocket for capturing bodily exudates. In these and other embodiments, it may be beneficial to direct the bodily exudates toward a central region of the article 10. This may be accomplished by bringing the pleat ends 121 closer together. Accordingly, in some embodiments, the pleat ends 121 may have a spacing 123 that is between about 5% and about 85%, or between about 5% and about 75%, or between about 5% and about 65%, or between about 5% and about 55% or between about 5% and about 45%, or between about 5% and about 35% of the pleat spacing 63 or 67. In some further embodiments the pleat ends 121 may connect, as shown with respect to the outer pleats 54 in FIG. 9. Although, in such embodiments, the outer pleats 54 may be considered to be one, single monolithic pleat the pleat end 121 may simply be the point along the pleat 54 that is disposed most proximate the front and or rear waist edges 22, 24.

Figure 10:
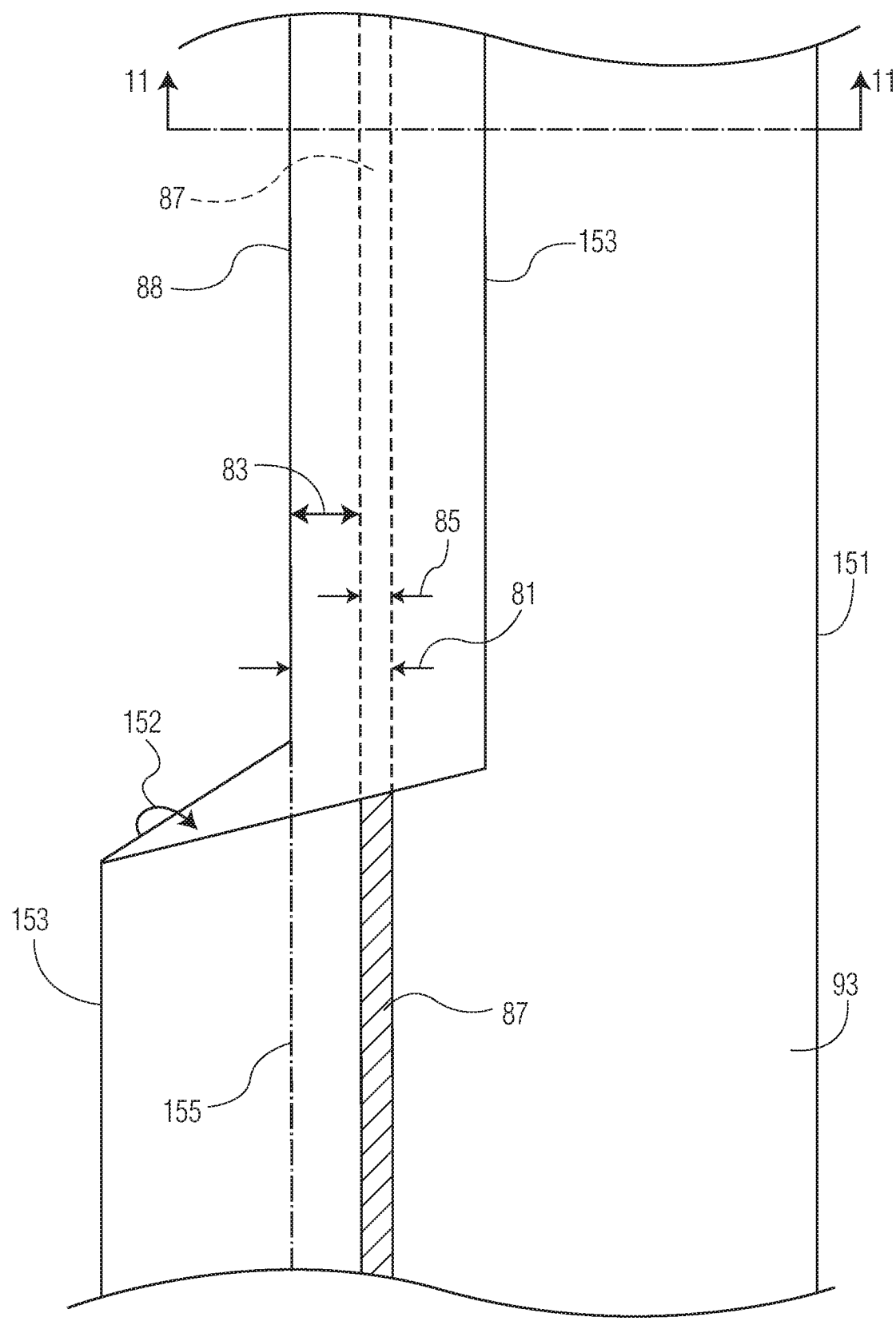
FIG. 10 is a top plan view of a continuous length of web material being folded to form one or more pleats.
Figure 11:
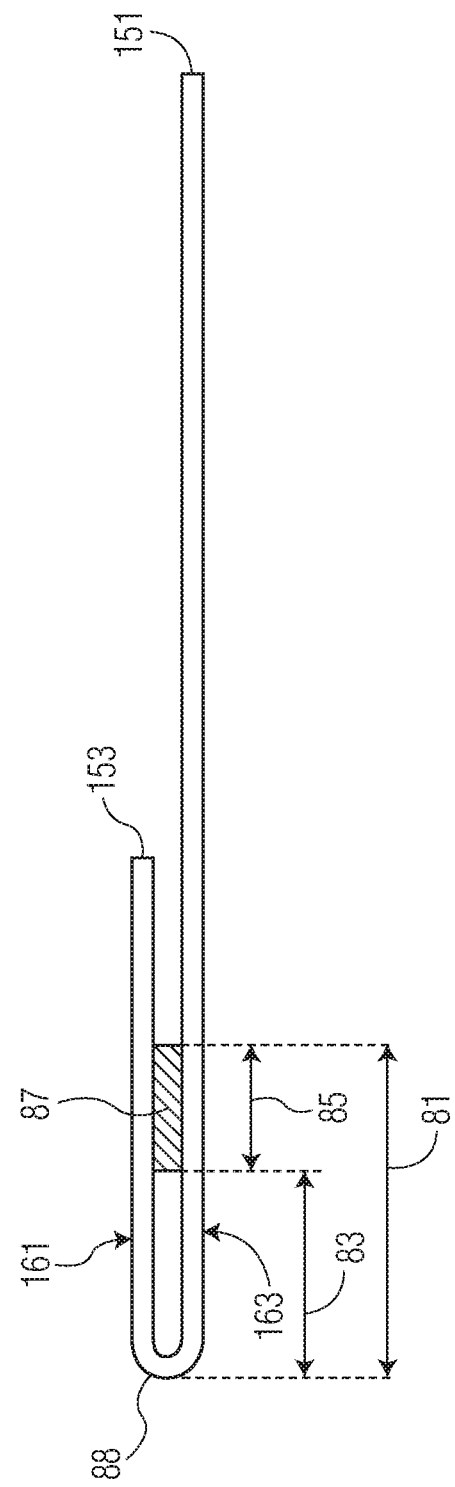
FIG. 11 is a cross-sectional view taken along line 11-11 from FIG. 10.

FIG. 10 depicts an exemplary pleat material 93 that may be used to form one or more pleats, and FIG. 11 is a cross-section of the pleat material 93 of FIG. 10 as viewed along line 11-11. As part of a continuous manufacturing process, the pleat material 93 may extend in a continuous manner in a machine direction and may extend in a cross-machine direction between a first transverse edge 151 and a second transverse edge 153.

To form one or more pleats 54, the pleat material 93 may be folded over upon itself, as indicated by arrow 152, along fold line 155 and forming fold 88. This folding of the pleat material 93 forms a pleat material top layer 161 and a pleat material bottom layer 163, as shown in FIG. 11. The pleat material 93 may then be bonded to itself, as indicated by bond 87 to form a pleat 54. In the example of FIG. 10, bond 87 is shown as an adhesive bead that is applied to the pleat material 93 prior to the folding of the pleat material 93. Although shown as applied to a top surface of the pleat material 93, the adhesive may be applied to a bottom surface of the pleat material 93 in other embodiments.

The distance between an inner edge of the bond 87 and the fold 88 represents the pleat height 81. Accordingly, the cross-machine direction width of the bond 87 corresponds to the lower pleat portion height 85, while the cross-machine direction width of the pleat material top layer 161 (or the pleat material bottom layer 163) between the bond 87 and the fold 88 corresponds to the upper pleat portion height 83.

Figure 12:
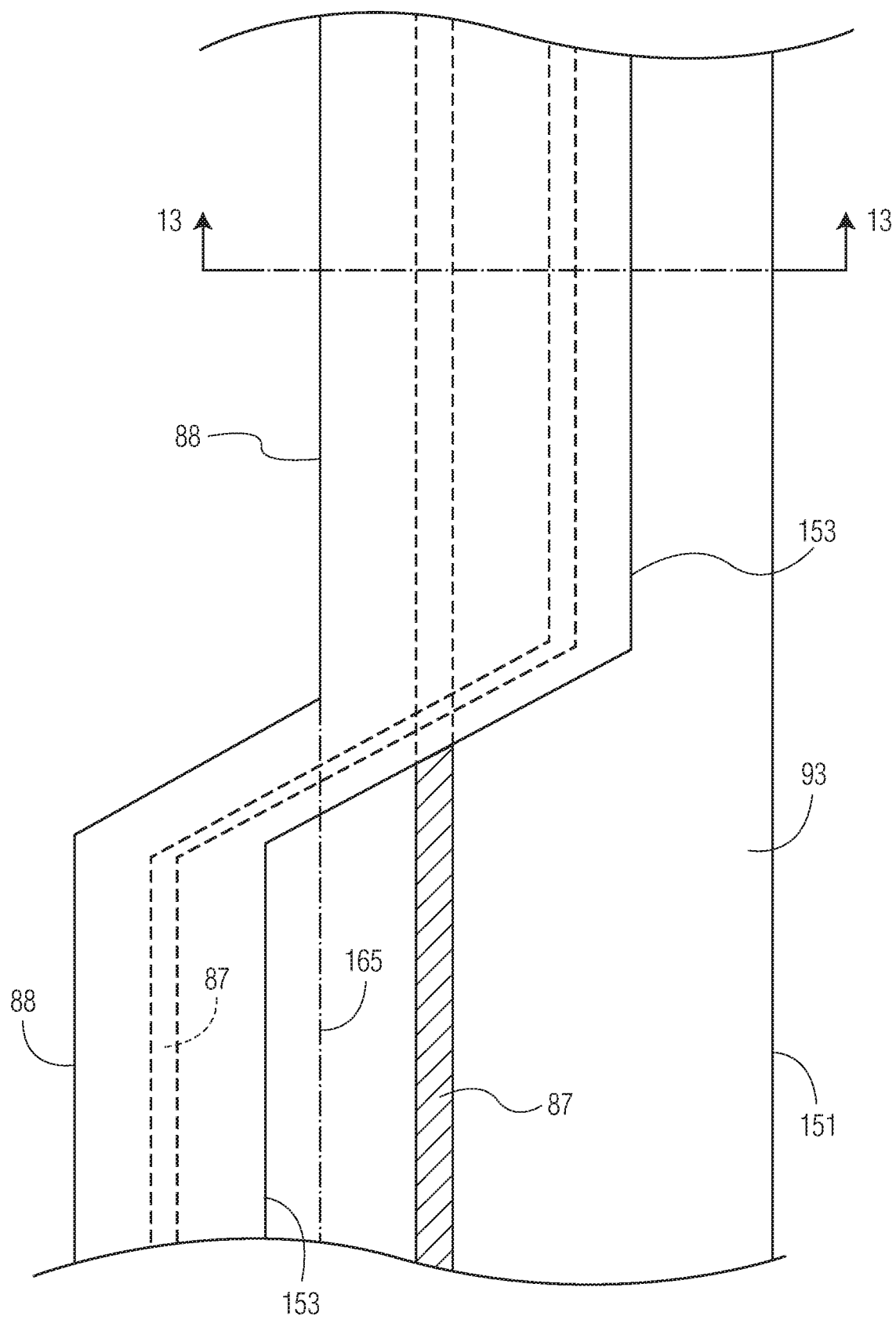
FIG. 12 is a top plan view of a continuous length of web material being folded to form one or more pleats.
Figure 13:
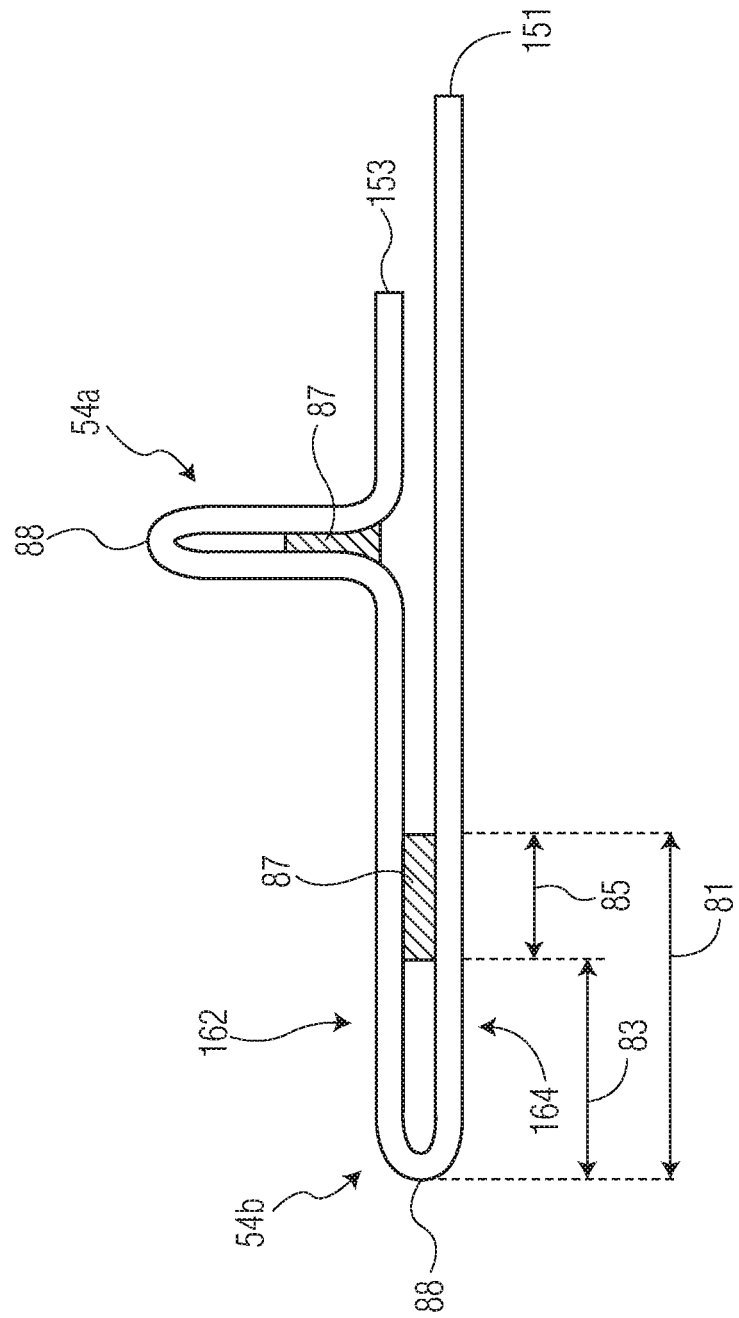
FIG. 13 is a cross-sectional view taken along line 13-13 from FIG. 12.

In some further embodiments, a second pleat 54 may be formed in the pleat material 93. FIGS. 12 and 13 depict the pleat material 93 of FIGS. 10 and 11 having a second pleat formed in the pleat material 93. These two pleats can be seen as pleats 54a, 54b in FIG. 13. To form the second pleat 54b in the material 93, the pleat material 93 may be further folded over upon itself along another fold line 165 and forming another fold 88, as shown in FIG. 12. In these embodiments, the folding along the fold line 165 may be accomplished without sandwiching the second transverse edge 153 between layers of the pleat material 93. For example, as can be seen in FIG. 13, in the folded configuration to form the second pleat 54b, the pleat material 93 still only comprises a pleat material top layer 162 and a pleat material lower layer 164, with the second transverse edge 153 disposed on top of the pleat material 93 and not between layers of the pleat material 93.

After folding along the fold line 165, the pleat material 93 may then be bonded to itself again, as indicated by the bond 87 located closest to the first transverse edge 151. In the example of FIG. 12, bond 87 is shown as an adhesive bead that is applied to the pleat material 93 prior to the folding of the pleat material 93. Although shown as applied to a top surface of the pleat material 93, the adhesive may be applied to a bottom surface of the pleat material 93 in other embodiments.

In relation to the pleat 54b, the distance between an inner edge of the bond 87 and the fold 88, as shown in FIG. 13, represents the pleat height 81. Accordingly, the cross-machine direction width of the bond 87 corresponds to the lower pleat portion height 85, while the cross-machine direction width of the pleat material top layer 161 (or the pleat material bottom layer 163) between the bond 87 and the fold 88 corresponds to the upper pleat portion height 83.

Figure 14:
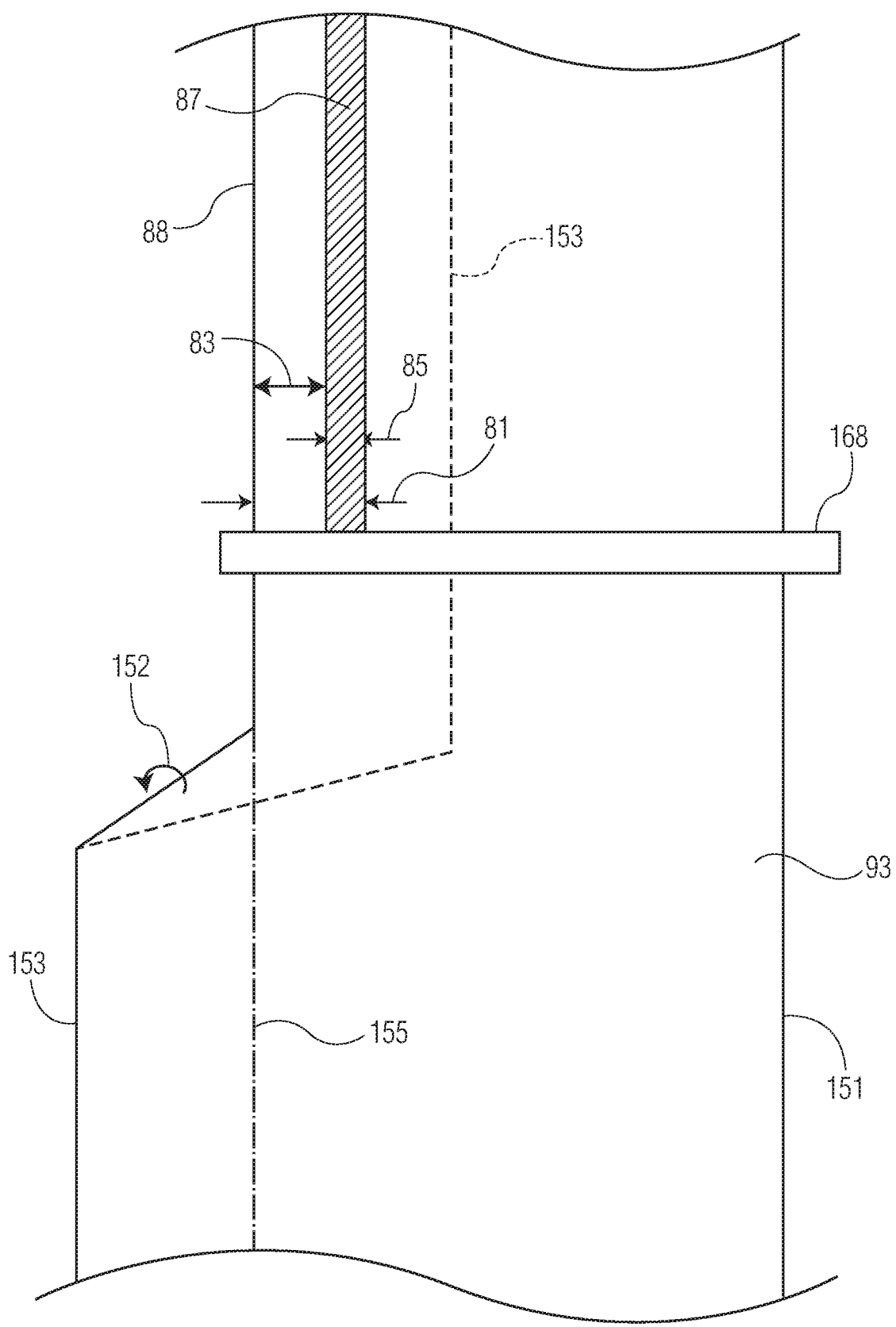
FIG. 14 is a top plan view of a continuous length of web material being folded to form one or more pleats.

FIG. 14 depicts another exemplary method to form the pleats 54. In the embodiment of FIG. 14, the pleat material 93 may be folded along fold line 155 in the direction indicated by arrow 152. After folding, the pleat material 93 may then be bonded to itself by bonder 168. In some embodiments, the bonder 168 may represent an ultrasonic bonder, of either of the rotary or blade-horn variety, configured to impart ultrasonic energy to the pleat material 93 to form the bond 87. In other embodiments, the bonder 168 may be configured to impart heat and/or pressure to the pleat material 93 to form the bond 87, as is known in the art.

Figure 15:
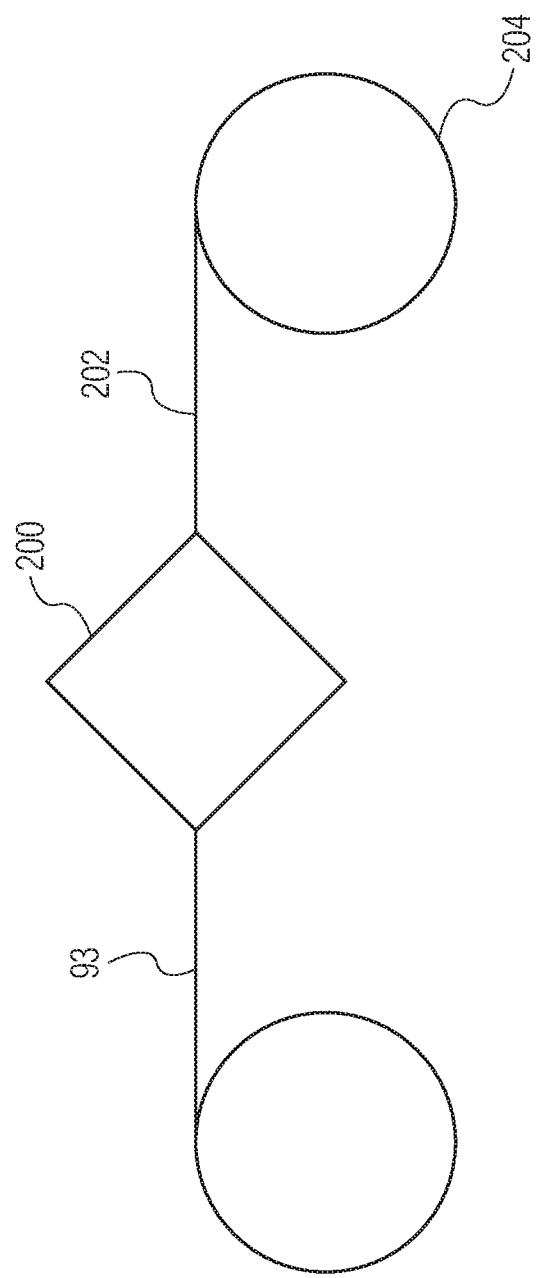
FIG. 15 is schematic view of an exemplary process for forming rolls of pleated material.

According to some embodiments, the pleat material 93 may be converted to comprise one or more pleats 54, according to aspects of the present disclosure, and then rolled up into individual rolls for transport. For example, FIG. 15 depicts one exemplary method of forming the pleat material 93 comprising one or more pleats 54. In the embodiment of FIG. 15, the pleat material 93 begins as a roll of material and is converted through converting process 200 to comprise one or more pleats 54. The converting process 200 may be any of the processes described with respect to the FIGS. 10-14. Once the pleats 54 are formed in the pleat material 93 by the converting process 200, the material 93 may be considered converted material 202. According to the embodiment of FIG. 15, the converted material 202 may then be rolled into individual rolls 204. Such individual rolls 204 of converted material 202 may then be used in common absorbent article manufacturing processes to form any of the articles 10 disclosed herein. According to some embodiments, the converted material 202 may represent still-folded pleat material 93. That is, the converted material 202 may look similar in cross-section to the embodiments of FIG. 11 or 13, wherein the bond(s) 87 have been formed, but the material is still in a folded configuration.

Figure 16:
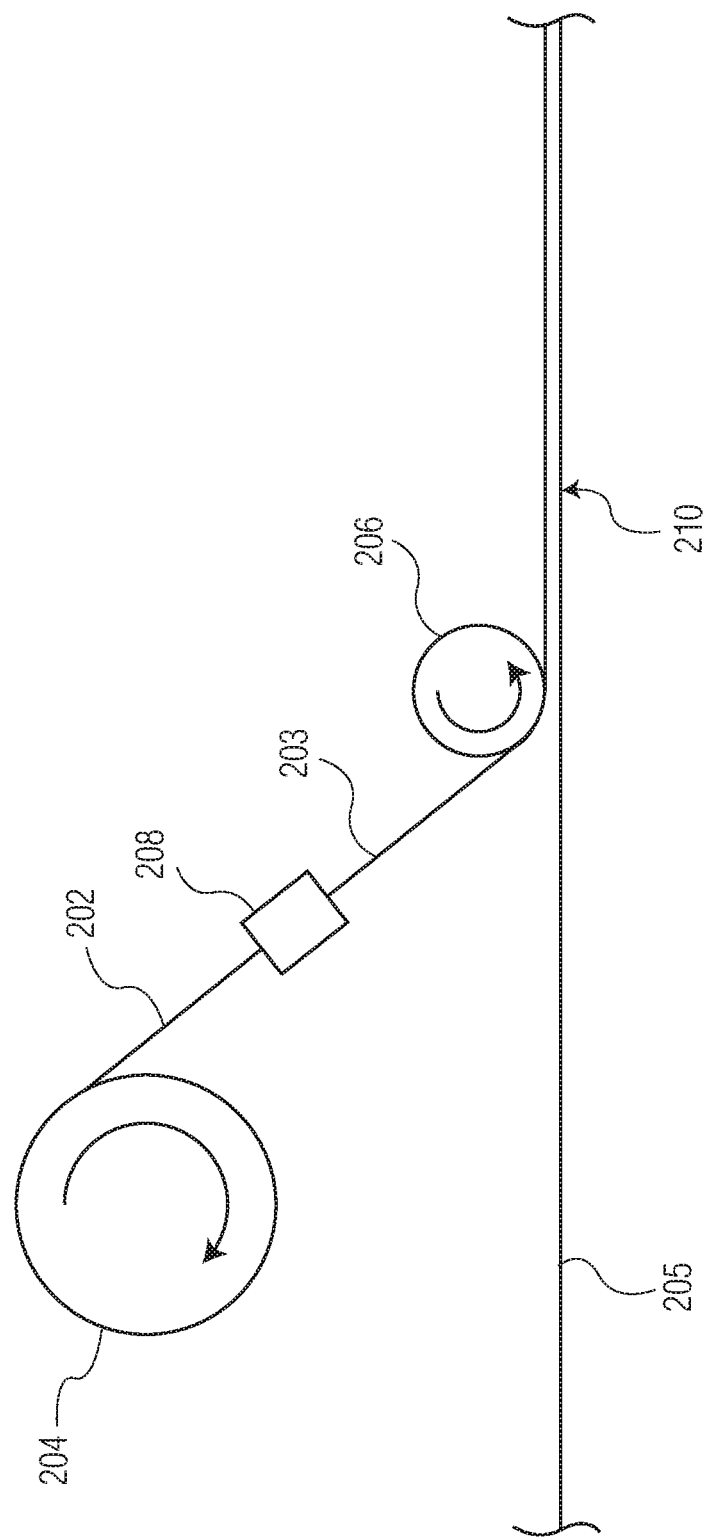
FIG. 16 is schematic view of an exemplary process for incorporating pleated materials into a process of forming individual absorbent articles.
Figure 17:
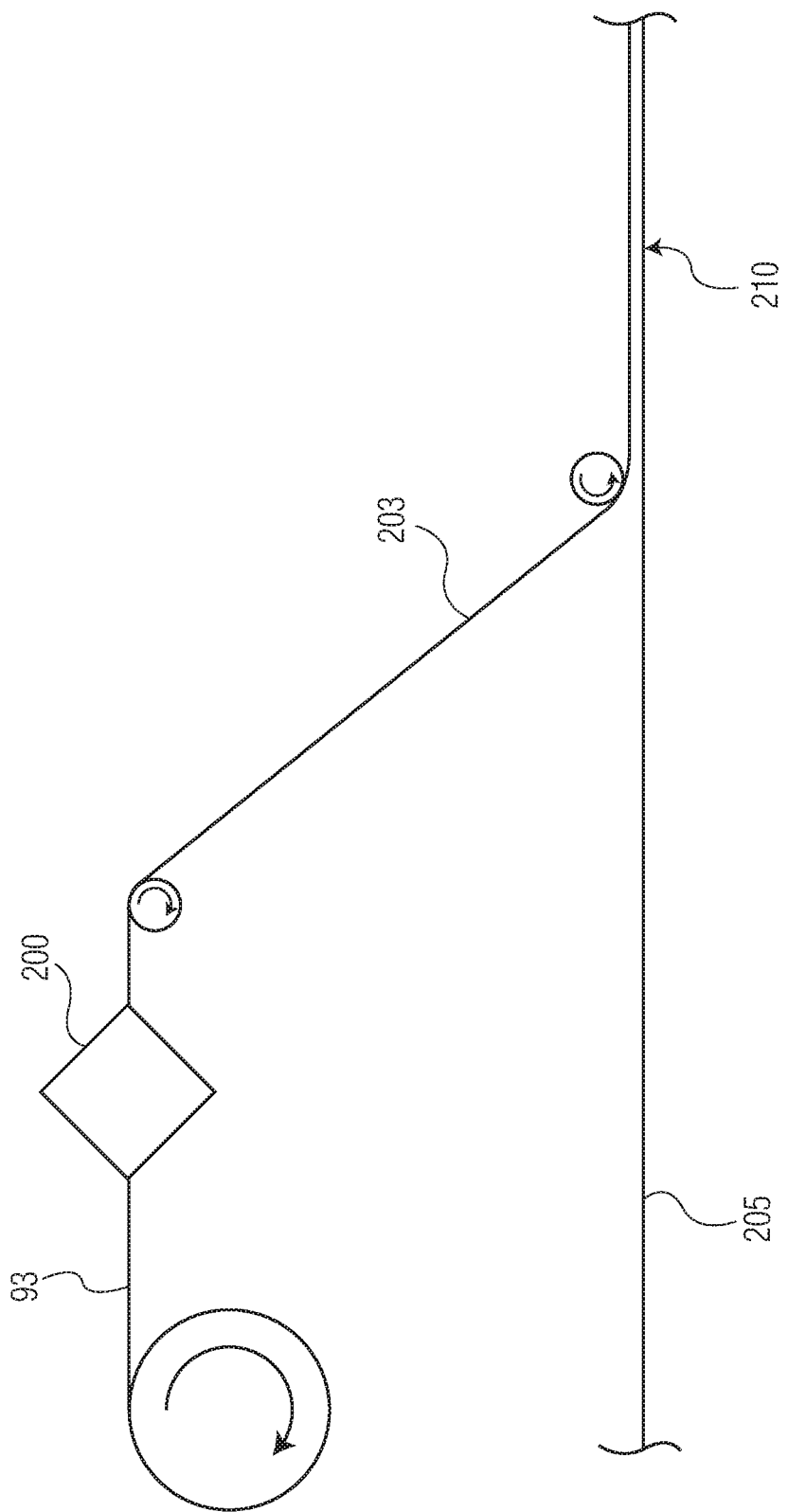
FIG. 17 is schematic view of an exemplary process for forming pleated materials as part of a process of forming individual absorbent articles.

FIGS. 16 and 17 depict exemplary methods of forming the absorbent articles 10 comprising the pleated materials of the present disclosure. In the embodiment of FIG. 16, a roll 204 of converted material 202 may be unrolled and unfolded at unfolding station 208, forming unfolded converted material 203. The unfolded converted material 203 may then pass by guide roll 206 and be attached to a continuous stream of absorbent article chassis 205, forming pleated continuous streams of absorbent article chassis 210. The pleated continuous streams of absorbent article chassis 210 may then be separated into individual absorbent articles according to known processes in the art.

In the embodiment of FIG. 17, instead of forming the converted material 202 off-line and bringing rolls 204 of the converted material 202 into an absorbent article manufacturing process as in the method of FIG. 16, the converted material 202 may be formed as part of a continuous absorbent article manufacturing process. For instance, the pleat material 93 begins as a roll of material and is converted through converting process 200 to comprise one or more pleats 54. The converting process 200 may be any of the processes described with respect to the FIGS. 10-14. In the embodiment of FIG. 17, the converting process 200 may further comprise a step of un-folding the converted material, forming unfolded converted material 203. The unfolded converted material 203 may then be attached to a continuous stream of absorbent article chassis 205, forming pleated continuous streams of absorbent article chassis 210. The pleated continuous streams of absorbent article chassis 210 may then be separated into individual absorbent articles according to known processes in the art.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

EMBODIMENTS

Embodiment 1: An absorbent article extending in a longitudinal direction and a lateral direction, the article may comprise a bodyside liner, an outer cover, an absorbent core disposed between the bodyside liner and the outer cover, and a pleat extending in the longitudinal direction and having a lower pleat portion and an upper pleat portion, the pleat having a pleat height, wherein the lower pleat portion has a greater stiffness than the upper pleat portion.

Embodiment 2: The absorbent article of embodiment 1, wherein the lower pleat portion may have a lower pleat portion height that is greater than about 5% and less than about 100% of the pleat height.

Embodiment 3: The absorbent article of any of the embodiments 1-2, wherein the lower pleat portion may have a lower pleat portion height that is between about 30% and about 95% of the pleat height.

Embodiment 4: The absorbent article of any of the embodiments 1-3, wherein the pleat has a height of between about 2 mm and about 15 mm.

Embodiment 5: The absorbent article of any of the embodiments 1-4, further comprising a pleat material that is folded to form the pleat, the pleat material being bonded to the bodyside liner.

Embodiment 6: The absorbent article of the embodiment 5, wherein the lower pleat portion comprises a region of the pleat where the folded pleat material is bonded together.

Embodiment 7: The absorbent article of the embodiment 6, wherein the folded pleat material is bonded together with adhesive disposed at a basis weight of between about 0.5 gsm and about 5 gsm.

Embodiment 8: The absorbent article of any of the embodiments 6-7, wherein the folded pleat material is bonded together without adhesive.

Embodiment 9: The absorbent article any of the embodiments 1-8, wherein the bodyside liner is folded to form the pleat.

Embodiment 10: The absorbent article of any of the embodiments 1-9, further comprising a plurality of pleats, the plurality of pleats having a spacing of between about 4 mm and about 15 mm between adjacent pleats.

Embodiment 11: An absorbent article extending in a longitudinal direction and a lateral direction, the article may comprise a bodyside liner, an outer cover, an absorbent core disposed between the bodyside liner and the outer cover, and a pleat material having a first side and a second side and being folded to form a pleat having a folded edge, the pleat material coupled to the bodyside liner with the folded edge disposed away from the bodyside liner and extending generally in the longitudinal direction, wherein the pleat comprises a lower pleat portion and an upper pleat portion and has a pleat height, the pleat material in the lower pleat portion being bonded together and the pleat material in the upper pleat portion being un-bonded.

Embodiment 12: The absorbent article of embodiment 11, wherein the pleat material in the lower pleat portion may be bonded together with adhesive.

Embodiment 13: The absorbent article of any of the embodiments 11-12, wherein the pleat material in the lower pleat portion may be bonded together without adhesive.

Embodiment 14: The absorbent article of any of the embodiments 11-13, wherein the pleat height is between about 4 mm and about 15 mm.

Embodiment 15: The absorbent article of any of the embodiments 11-14, wherein the lower pleat portion has a lower pleat portion height that is between about 30% and about 95% of the pleat height Embodiment 16: The absorbent article of any of the embodiments 11-15, wherein the pleat material has a basis weight of between about 5 gsm and about 150 gsm.

Embodiment 17: The absorbent article of any of the embodiments 11-16, further comprising a plurality of pleats, the plurality of pleats having a spacing of between about 4 mm and about 15 mm between adjacent pleats.

Embodiment 18: An absorbent article extending in a longitudinal direction and a lateral direction, the article may comprise a bodyside liner, an outer cover, an absorbent core disposed between the bodyside liner and the outer cover, and a plurality of pleats extending generally in the longitudinal direction, each of the plurality of pleats having a pleat height of between about 2 mm and about 15 mm and spaced a lateral spacing distance from adjacent pleats of between about 2 mm and about 15 mm, wherein each of the plurality of pleats has a lower pleat portion and an upper pleat portion, the lower pleat portion having a greater stiffness than the upper pleat portion.

Embodiment 19: The absorbent article of the embodiment 18, further comprising a longitudinally extending centerline and a pair of longitudinally extending containment flaps, each of the pair of containment flaps disposed on opposite sides of the longitudinally extending centerline, wherein each of the containment flaps are attached to a body-facing surface of the article and comprise a base portion and a projection portion, the projection portions spaced apart a projection spacing distance, and wherein each of the plurality of pleats may be disposed at least a threshold distance away from the projection portions of the containment flaps, the threshold distance being equal to the height of each pleat.

Embodiment 20: The absorbent article of any of the embodiments 18-19, wherein end portions of at least some of the plurality of the pleats may curve or angle toward a longitudinal centerline of the article.

Embodiment 21: The absorbent article of any of the embodiments 18-20, wherein the lower pleat portions may have lower pleat portion heights that are between about 30% and about 95% of the pleat height.

Embodiment 22: The absorbent article of any of the embodiments 18-21, wherein each of the plurality of pleats comprises a pleat material forming a fold, and wherein portions of each pleat material may be bonded together forming the lower pleat portions of the plurality of pleats.

Embodiment 23: The absorbent article of any of the embodiments 18-22, wherein the portions of each pleat material may be bonded together without adhesive.

Embodiment 24: The absorbent article of any of the embodiments 18-23, wherein the bodyside liner comprises the pleats.

Embodiment 25: A method for forming an absorbent article which may comprise moving a substrate material having a transverse width dimension in a machine direction, folding the substrate material along a first fold line extending in the machine direction forming a substrate material top layer and a substrate material bottom layer and a first folded transverse material edge, bonding the substrate material top layer to the substrate material bottom layer a bonding distance away from the first folded transverse material edge, unfolding the substrate material, and attaching the substrate material to an absorbent article chassis comprising a back sheet and an absorbent core such that the substrate material sandwiches the absorbent core between the substrate material and the back sheet.

Embodiment 26: The method of embodiment 25, further comprising winding the folded substrate material into a roll and unwinding the substrate material from the roll prior to unfolding the substrate material.

Embodiment 27: The method of any of the embodiments 25-26, further comprising folding the substrate material along a second fold line extending in the machine direction forming a substrate material top layer and a substrate material bottom layer and a second folded transverse material edge, and bonding the substrate material top layer to the substrate material bottom layer a bonding distance away from the second folded transverse material edge.

Embodiment 28: The method of any of the embodiments 25-27, wherein the bonding distance may be between about 2 mm and about 15 mm from the first folded transverse material edge.

Embodiment 29: The method of any of the embodiments 16-28, wherein bonding the substrate material top layer to the substrate material bottom layer may comprise forming a bond between the substrate material top layer to the substrate material bottom layer having a transverse bond length dimension and wherein the transverse bond length dimension is between about 30% and about 95% of the bonding distance.

Embodiment 30: The method of any of the embodiments 25-29, wherein the step of bonding the substrate material top layer to the substrate material bottom layer may comprise bonding the substrate material top layer to the substrate material bottom layer with adhesive applied at between about 0.5 gsm and about 5.0 gsm.

Embodiment 31: The method of any of the embodiments 25-30, wherein the step of bonding the substrate material top layer to the substrate material bottom layer comprises bonding the substrate material top layer to the substrate material bottom layer without adhesive.

What is claimed is:

1. An absorbent article extending in a longitudinal direction and a lateral direction, the article comprising:
    a bodyside liner;
    an outer cover;
    an absorbent core disposed between the bodyside liner and the outer cover; and
    a pleat extending above the bodyside liner and having a pleat height, the pleat further extending along the longitudinal direction and having a lower pleat portion and an upper pleat portion,
    wherein each portion of the upper pleat portions has a lower stiffness than a stiffness of the lower pleat portion.

2. The absorbent article of claim 1, wherein the lower pleat portion has a lower pleat portion height that is greater than about 5% and less than about 100% of the pleat height.

3. The absorbent article of claim 1, wherein the lower pleat portion has a lower pleat portion height that is between about 30% and about 95% of the pleat height.

4. The absorbent article of claim 1, wherein the pleat has a height of between about 2 mm and about 15 mm.

5. The absorbent article of claim 1, further comprising a pleat material that is folded to form the pleat, the pleat material being bonded to the bodyside liner.

6. The absorbent article of claim 5, wherein the lower pleat portion comprises a region of the pleat where the folded pleat material is bonded together.

7. The absorbent article of claim 6, wherein the folded pleat material is bonded together with adhesive disposed at a basis weight of between about 0.5 gsm and about 5 gsm.

8. The absorbent article of claim 6, wherein the folded pleat material is bonded together without adhesive.

9. The absorbent article claim 1, wherein the bodyside liner is folded to form the pleat.

10. The absorbent article of claim 1, further comprising a plurality of pleats, the plurality of pleats having a spacing of between about 4 mm and about 15 mm between adjacent pleats.

11. An absorbent article extending in a longitudinal direction and a lateral direction, the article comprising:
    a bodyside liner;
    an outer cover;
    an absorbent core disposed between the bodyside liner and the outer cover; and
    a pleat material having a first side and a second side and being folded to form a pleat having a folded edge, the pleat material coupled to the bodyside liner with the folded edge disposed away from the bodyside liner and extending generally in the longitudinal direction,
    wherein the pleat comprises:
        a first pleat wall extending from a base of the pleat to the folded edge of the pleat and a second pleat wall extending from the base of the pleat to the folded edge of the pleat,
        a lower pleat portion comprising a portion of the first pleat wall and the second pleat wall and an upper pleat portion comprising a portion of the first pleat wall and the second pleat wall, and
        a pleat height,
        wherein the first pleat wall in the lower pleat portion is bonded together with the second pleat wall in the lower pleat portion and wherein the first pleat wall in the upper pleat portion is un-bonded to the second pleat wall.

12. The absorbent article of claim 11, wherein the pleat material in the lower pleat portion is bonded together with adhesive.

13. The absorbent article of claim 11, wherein the pleat material in the lower pleat portion is bonded together without adhesive.

14. The absorbent article of claim 11, wherein the pleat height is between about 4 mm and about 15 mm.

15. The absorbent article of claim 11, wherein the lower pleat portion has a lower pleat portion height that is between about 30% and about 95% of the pleat height.

16. The absorbent article of claim 11, wherein the pleat material has a basis weight of between about 5 gsm and about 150 gsm.

17. The absorbent article of claim 11, further comprising a plurality of pleats, the plurality of pleats having a spacing of between about 4 mm and about 15 mm between adjacent pleats.

18. An absorbent article extending in a longitudinal direction and a lateral direction, the article comprising:
    a bodyside liner;
    an outer cover;
    an absorbent core disposed between the bodyside liner and the outer cover; and
    a plurality of pleats extending above the bodyside liner and having a pleat height of between about 2 mm and about 15 mm, the plurality of pleats further extending generally in the longitudinal direction with each of the plurality of pleats spaced a lateral spacing distance from adjacent pleats of between about 2 mm and about 15 mm,
    wherein each of the plurality of pleats has a lower pleat portion and an upper pleat portion and wherein each portion of the upper pleat portion has a lower stiffness than a stiffness of the lower pleat portion.

19. The absorbent article of claim 18, further comprising a longitudinally extending centerline and a pair of longitudinally extending containment flaps, each of the pair of containment flaps disposed on opposite sides of the longitudinally extending centerline, wherein each of the containment flaps are attached to a body-facing surface of the article and comprise a base portion and a projection portion, the projection portions spaced apart a projection spacing distance, and wherein each of the plurality of pleats are disposed at least a threshold distance away from the projection portions of the containment flaps, the threshold distance being equal to the height of each pleat.

20. The absorbent article of claim 18, wherein end portions of at least some of the plurality of the pleats curve or angle toward a longitudinal centerline of the article.

\* \* \* \* \*